US011040127B2

(12) United States Patent
Simmons et al.

(10) Patent No.: US 11,040,127 B2
(45) Date of Patent: Jun. 22, 2021

(54) ABDOMINAL DRESSING WITH MECHANISM FOR FASCIAL CLOSURE

(71) Applicant: KCI LICENSING, INC., San Antonio, TX (US)

(72) Inventors: Tyler H. Simmons, San Antonio, TX (US); David R. Mercer, San Antonio, TX (US); David Schroeder, San Antonio, TX (US); Colin J. Hall, Poole (GB)

(73) Assignee: KCI LICENSING, INC., San Antonio, TX (US)

( * ) Notice: Subject to any disclaimer, the term of this patent is extended or adjusted under 35 U.S.C. 154(b) by 455 days.

(21) Appl. No.: 15/948,376

(22) Filed: Apr. 9, 2018

(65) Prior Publication Data

US 2019/0307935 A1  Oct. 10, 2019

(51) Int. Cl.
*A61M 1/00* (2006.01)
*A61F 13/02* (2006.01)
(Continued)

(52) U.S. Cl.
CPC ....... *A61M 1/0088* (2013.01); *A61F 13/0206* (2013.01); *A61F 13/0216* (2013.01);
(Continued)

(58) Field of Classification Search
CPC .. A61M 1/0088; A61M 1/0084; A61M 1/009; A61M 1/0092; A61M 1/0094;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Partial International Search Report in International Application No. PCT/US2019/025979, dated Jun. 25, 2019.

(Continued)

*Primary Examiner* — Jan Christopher L Merene
*Assistant Examiner* — Matthew Standard
(74) *Attorney, Agent, or Firm* — Foley & Lardner LLP

(57) ABSTRACT

A system for treating a deep abdominal wound. The system includes a wound dressing. The wound dressing includes a visceral-protective layer, a compressive layer, and a sealing layer. The visceral-protective layer is configured to be positioned in an open abdomen. The compressive layer is configured to be disposed proximate to the visceral-protective layer. The compressive layer includes a pattern of voids configured for anisotropic collapse of the compressive layer when under negative pressure. The sealing layer is configured to form a sealed space in the open abdomen. A negative pressure source configured to provide negative pressure to the compressive layer.

12 Claims, 19 Drawing Sheets

(51) Int. Cl.
  *B29C 65/00*    (2006.01)
  *B29C 43/18*    (2006.01)
  *A61L 15/42*    (2006.01)
  *A61L 15/26*    (2006.01)
  *B29C 51/26*    (2006.01)
  *B29C 65/48*    (2006.01)
  *B29C 65/10*    (2006.01)
  *B29C 65/78*    (2006.01)
  *B29K 75/00*    (2006.01)
  *B29K 105/04*   (2006.01)
  *B29L 31/00*    (2006.01)

(52) U.S. Cl.
  CPC ............ *A61L 15/26* (2013.01); *A61L 15/425* (2013.01); *B29C 43/18* (2013.01); *B29C 51/268* (2013.01); *B29C 65/106* (2013.01); *B29C 65/48* (2013.01); *B29C 65/7802* (2013.01); *B29C 66/41* (2013.01); *B29C 66/727* (2013.01); *B29C 66/7315* (2013.01); *B29C 66/7352* (2013.01); *B29C 66/73161* (2013.01); *A61M 1/0084* (2013.01); *A61M 2205/0216* (2013.01); *A61M 2207/00* (2013.01); *B29K 2075/00* (2013.01); *B29K 2105/04* (2013.01); *B29K 2995/0046* (2013.01); *B29K 2995/0053* (2013.01); *B29K 2995/0072* (2013.01); *B29K 2995/0097* (2013.01); *B29L 2031/753* (2013.01)

(58) Field of Classification Search
  CPC .. A61M 1/0096; A61M 1/0058; A61M 27/00; A61L 26/00; A61L 15/26; A61L 15/425; A61L 15/18; B29C 43/18; B29C 43/268; B29C 43/106; B29C 43/48; B29C 43/7802
  See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,867,206 B2 * | 1/2011 | Lockwood | A61M 1/0058 604/289 |
| 8,114,126 B2 | 2/2012 | Heaton et al. | |
| 8,142,419 B2 | 3/2012 | Heaton et al. | |
| 8,192,409 B2 | 6/2012 | Hardman et al. | |
| 8,197,467 B2 | 6/2012 | Heaton et al. | |
| 8,608,776 B2 | 12/2013 | Coward et al. | |
| 8,936,618 B2 | 1/2015 | Sealy et al. | |
| 9,421,132 B2 | 8/2016 | Dunn | |
| 9,962,295 B2 | 5/2018 | Dunn et al. | |
| 10,117,782 B2 | 11/2018 | Dagger et al. | |
| 10,130,520 B2 | 11/2018 | Dunn et al. | |
| 10,159,771 B2 | 12/2018 | Hartwell et al. | |
| 10,179,073 B2 | 1/2019 | Hartwell et al. | |

(56) References Cited

U.S. PATENT DOCUMENTS

| | | | |
|---|---|---|---|
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0209574 A1* | 9/2005 | Boehringer | A61F 13/00068 604/289 |
| 2009/0030383 A1 | 1/2009 | Larsen et al. | |
| 2009/0227969 A1 | 9/2009 | Jaeb et al. | |
| 2011/0213319 A1 | 9/2011 | Blott et al. | |
| 2011/0224634 A1 | 9/2011 | Locke et al. | |
| 2015/0032031 A1 | 1/2015 | Hartwell | |
| 2015/0216732 A1* | 8/2015 | Hartwell | A61F 13/00021 604/319 |
| 2015/0231314 A1 | 8/2015 | Robinson et al. | |
| 2015/0320603 A1 | 11/2015 | Locke et al. | |
| 2016/0045648 A1 | 2/2016 | Locke et al. | |
| 2016/0166740 A1 | 6/2016 | Hartwell | |
| 2017/0007462 A1* | 1/2017 | Hartwell | A61M 1/0088 |
| 2017/0007752 A1 | 1/2017 | Freedman et al. | |
| 2017/0209641 A1 | 7/2017 | Mercer et al. | |
| 2019/0105202 A1 | 4/2019 | Dunn et al. | |
| 2019/0209383 A1 | 7/2019 | Hartwell et al. | |
| 2019/0231599 A1 | 8/2019 | Dagger et al. | |
| 2019/0231945 A1 | 8/2019 | Hartwell et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3 269 404 A1 | 1/2018 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2012/106590 A2 | 8/2012 |
| WO | WO-2013/066694 A2 | 5/2013 |
| WO | WO-2013/175309 A1 | 11/2013 |
| WO | WO-2015/008054 A1 | 1/2015 |
| WO | WO-2015/110409 A1 | 7/2015 |
| WO | WO-2015/110410 A1 | 7/2015 |
| WO | WO-2016/176513 A1 | 11/2016 |
| WO | WO-2017/063036 A1 | 4/2017 |
| WO | WO-2018/013242 A1 | 1/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," In II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract")
V.A.C.® Therapy Clinical Guidelines: A Reference Source for Clinicians; Jul. 2007.

* cited by examiner

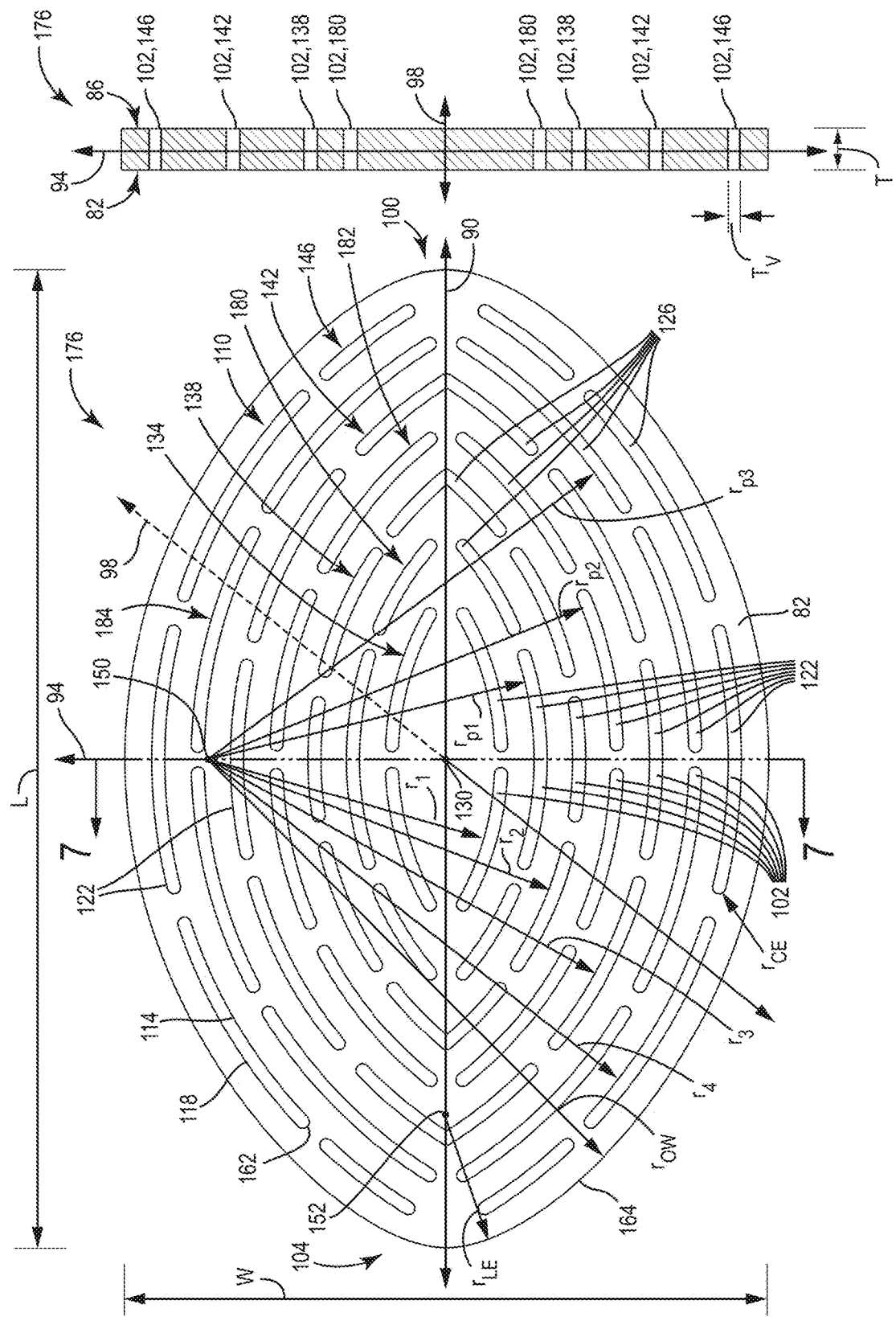

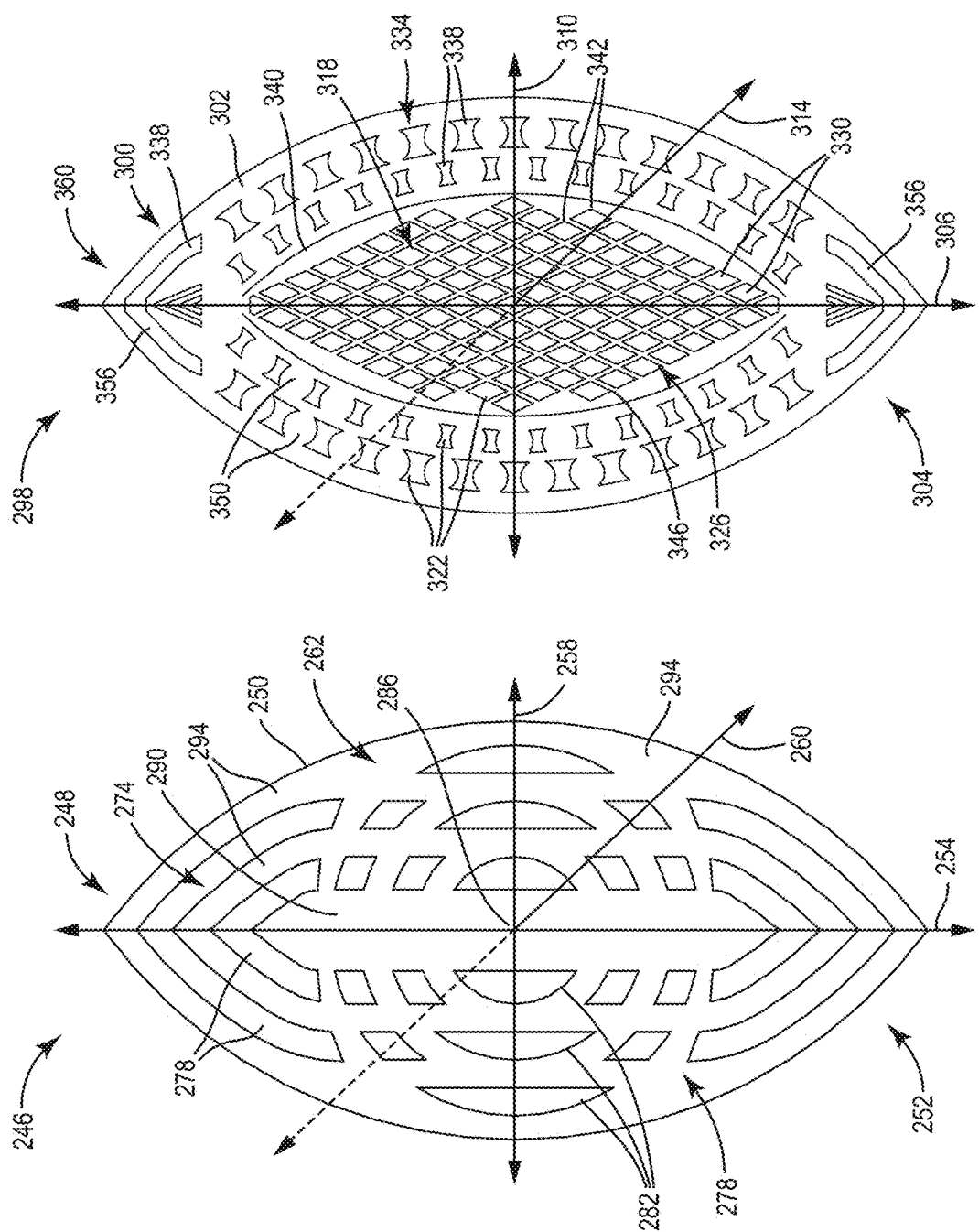

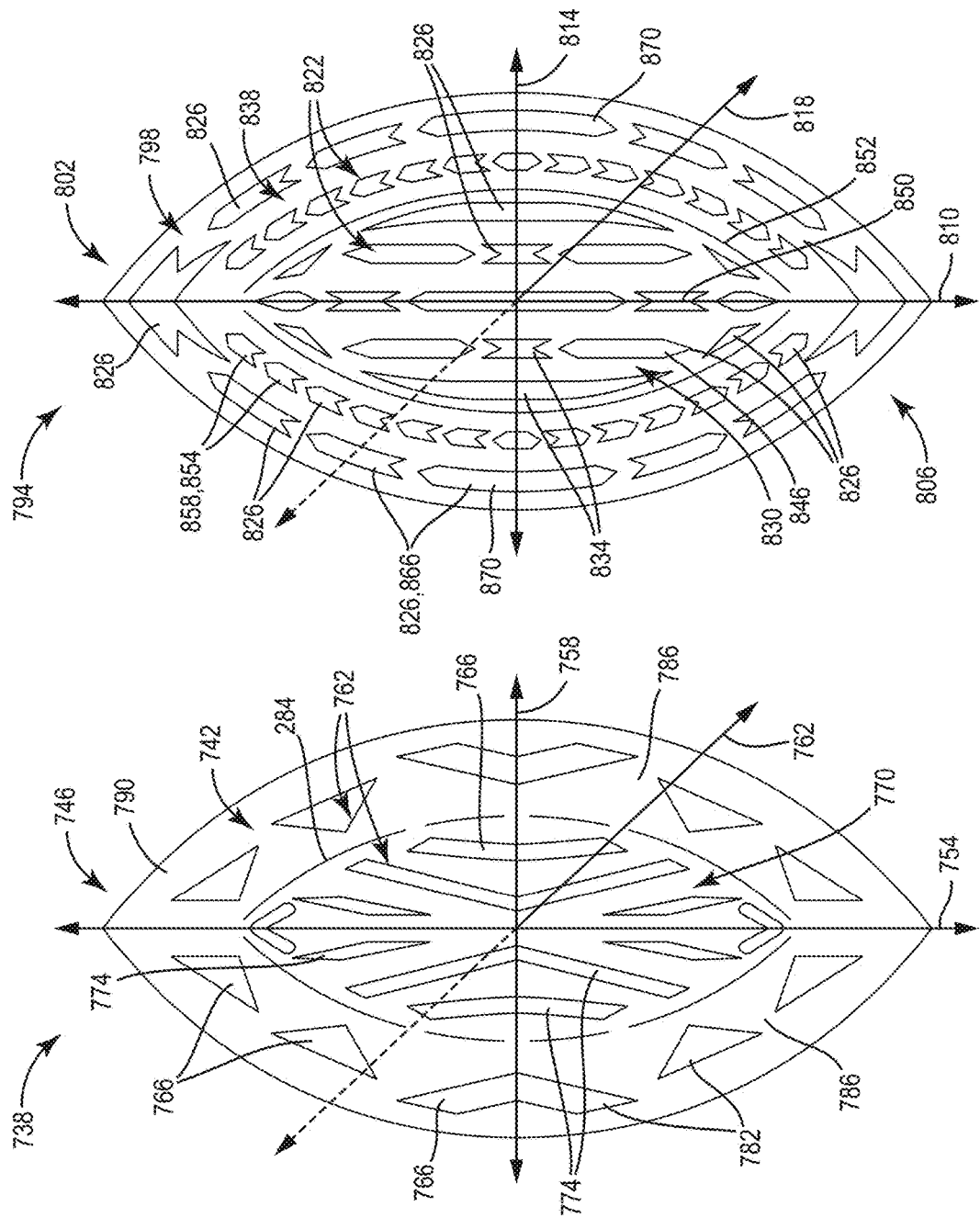

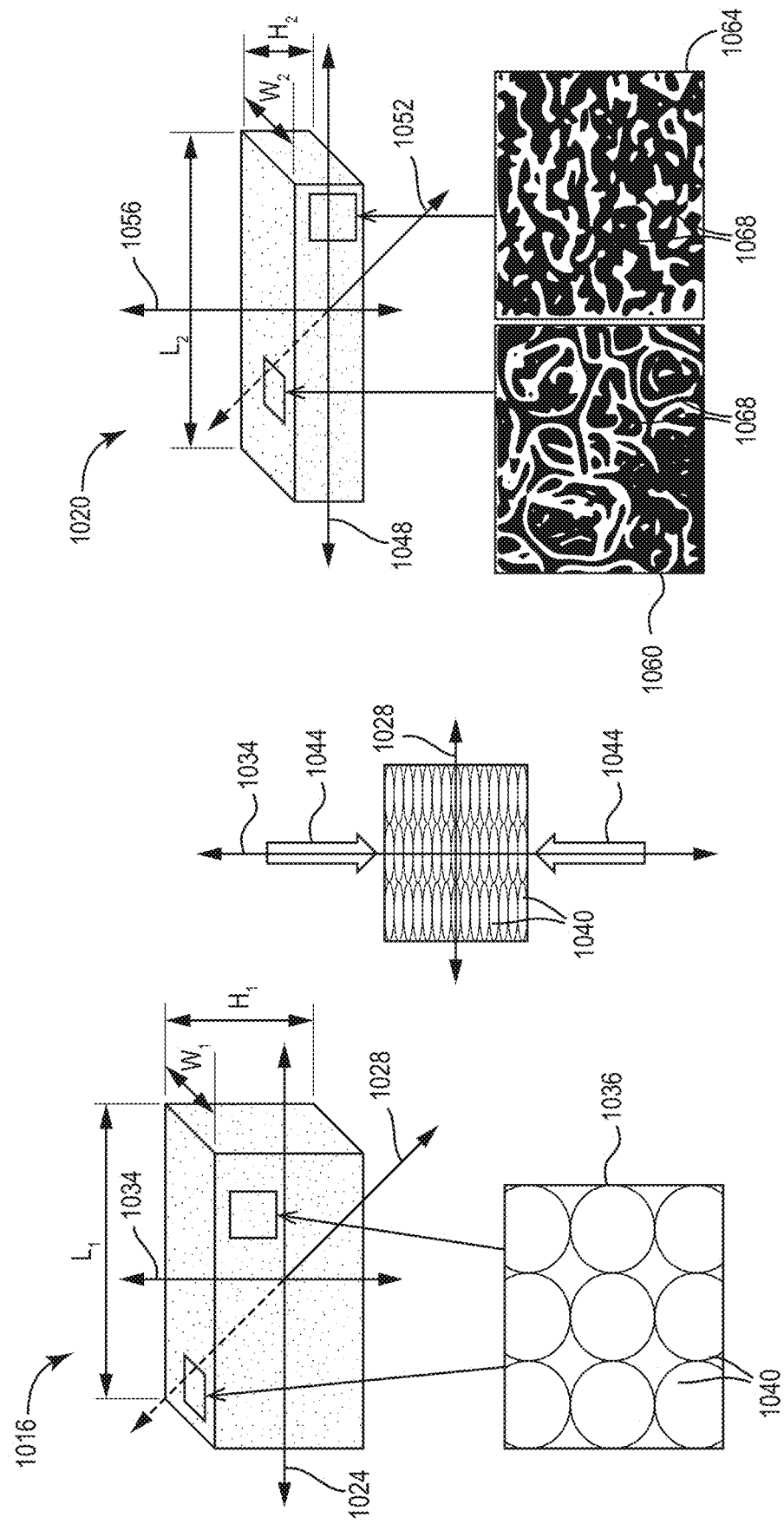

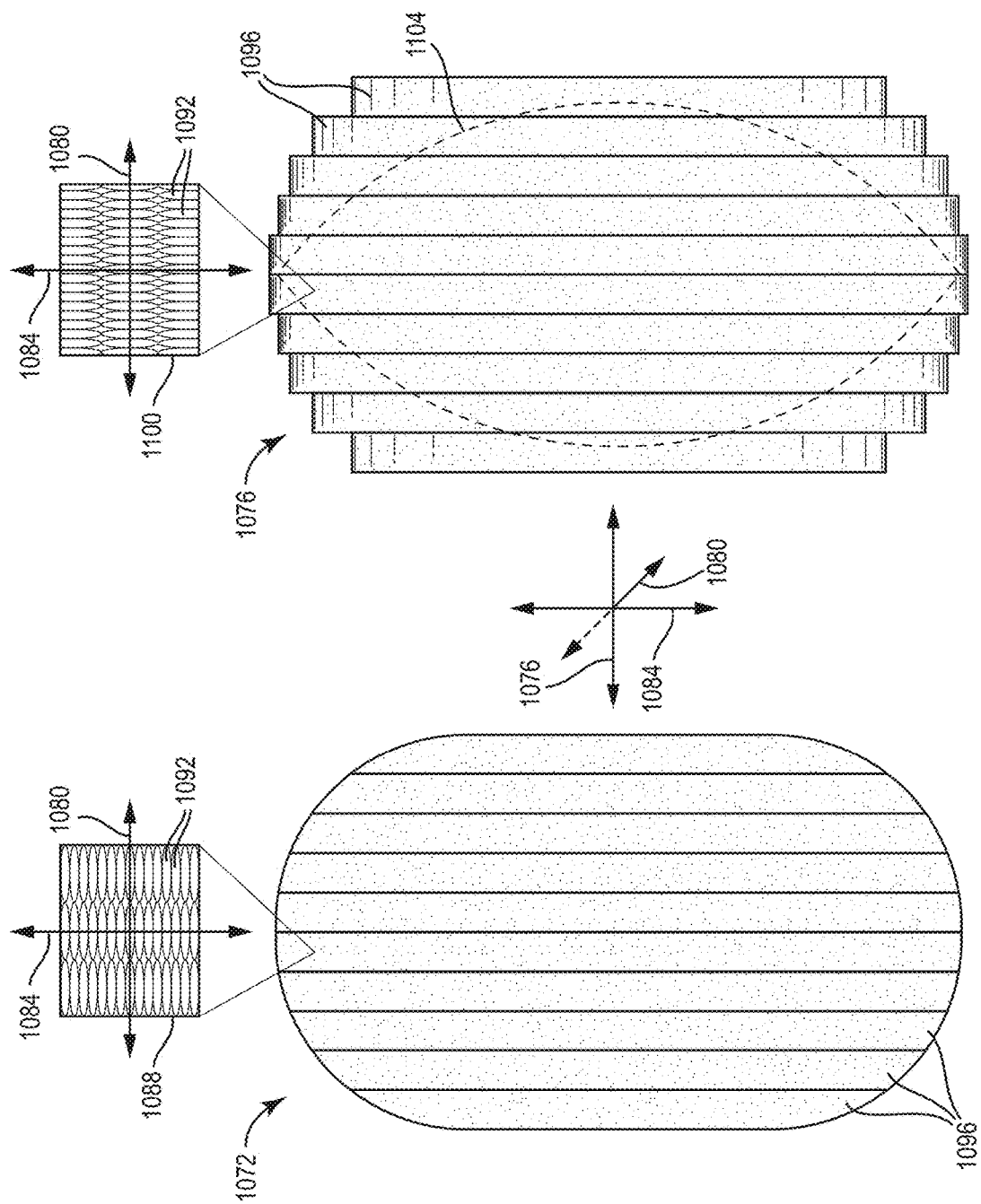

ABDOMINAL DRESSING WITH MECHANISM FOR FASCIAL CLOSURE

BACKGROUND

The present disclosure relates generally to a wound treatment system, and more particularly, to a wound therapy system contoured to provide negative pressure wound therapy (NPWT) to a fascial incision in an open abdomen.

Negative pressure wound therapy is a type of wound therapy that involves applying a negative pressure to a wound site to promote wound healing. NPWT applies negative pressure to the wound to drain fluids from the wound as the wound heals. NPWT can be used to treat deep abdominal wounds due to abdominal laparotomies, which are used to gain access to the abdominal cavity for surgery and/or to relieve intra-abdominal pressure by allowing the bowels to expand. Such deep abdominal wounds require cutting of the fascial layer, which is a thin, fibrous layer of tissue located beneath the abdominal muscles that holds the abdominal contents (e.g., internal organs and the bowels) together. In some instances, the laparotomy incision is not immediately closed, resulting in an "open abdomen." Under such conditions, the fascia can retract laterally toward the patient's paracolic gutters (e.g., open space on the sides of the abdominal cavity), which can make it difficult to secure the cut ends of the fascial layer together (e.g., with staples or sutures) after surgery. Failure to secure the cut ends of the fascial layer together can result in ventral hernia. Existing methods for pulling the cut ends of the fascial layer together can result in damage to the fascial layer, which is difficult to repair and can further complicate closure of the fascial layer. Furthermore, staples and/or sutures are currently used to hold the cut ends of the fascia together under the open abdomen conditions. Removal of the staples and/or sutures for further surgery can cause damage to the cut ends of the fascial layer.

SUMMARY

One embodiment of the present disclosure is a system for treating a deep abdominal wound. The system includes a wound dressing and a negative pressure source. The wound dressing includes a visceral-protective layer, a compressive layer, and a sealing layer. In use, the visceral-protective layer is configured to engage a fascial incision and cover and protects the abdominal contents. The compressive layer is configured to be disposed atop or proximate to the visceral-protective layer. The compressive layer has a pattern of voids configured for anisotropic collapse of the compressive layer under negative pressure. For example, the compressive layer collapses in a first direction and resists collapse (relative to the first direction) in a second direction substantially perpendicular to the first direction when subjected to a negative pressure. The sealing layer is affixed to the patient's skin, over and around the patient's open incision, in order to create a sealed space (in the open abdomen). The negative pressure source is fluidly coupled to the sealed space (e.g., via tubing from the negative pressure source to an aperture in the sealing layer) and provides negative pressure to the sealed space.

Another embodiment of the present disclosure is a compressive layer for use with a deep abdominal wound dressing. The compressive layer includes a body formed of a material having a plurality of voids configured to provide a first modulus of elasticity in a first direction and a second modulus of elasticity in a second direction substantially perpendicular to the first direction. The first modulus of elasticity is smaller than the second modulus of elasticity so that the body is configured to compress in the first direction and to resist compression in the second direction. The body includes a plurality of voids shaped and/or positioned for lateral compression in the first direction and radial compression in the second direction.

Another embodiment of the present disclosure is a system for treating a deep abdominal wound. The system includes a negative pressure source and a wound dressing. The negative pressure source is configured to provide a negative pressure. The wound dressing defines a longitudinal axis. The wound dressing includes a compressive layer configured to resist compression in a direction normal to the wound dressing. The compressive layer a includes pattern of voids configured to collapse in a greater amount in a substantially lateral direction than in a substantially vertical direction and a substantially longitudinal direction under the negative pressure, thereby exerting the lateral compressive force towards the longitudinal axis.

Another embodiment of the present disclosure is a method for forming a compressive layer for a deep abdominal wound dressing. The method includes heating a foam layer. The foam layer has substantially isotropic material properties. The method further includes applying a compressive force to the foam layer to increase a density of the foam layer in a direction of the compressive force to cause anisotropy in the foam layer by generating a first modulus of elasticity in a first direction corresponding to a direction of the applied force and a second modulus of elasticity in a second direction substantially perpendicular to the first direction. The method further includes cutting the foam layer in a direction substantially perpendicular to the direction of the compressive force. The method further includes rotating the pieces of the foam layer, securing adjacent pieces of the foam layer, and forming a compressive layer from the foam layer.

Another embodiment of the present disclosure is a wound dressing for a deep abdominal wound. The wound dressing includes a compression portion formed of an anisotropic material having a first modulus of elasticity in a first direction and second modulus of elasticity in a second direction. The first modulus of elasticity is smaller than the second modulus of elasticity so that the body is configured to collapse in the first direction and resist compression in the first direction. The wound dressing further includes a manifold portion surrounding the compression portion configured to provide negative pressure and/or add or remove fluids.

In some embodiments, the compression portion defines a longitudinal axis and includes a pattern of voids configured to collapse in the first direction under a negative pressure, thereby exerting a lateral compressive force towards the longitudinal axis.

In some embodiments, the first direction is a substantially lateral direction and the second direction is a substantially vertical direction.

Another embodiment of the present disclosure is a wound therapy system for a deep abdominal wound. The wound dressing includes a compression portion, a manifold portion, and a negative pressure source. The compression portion is formed of an anisotropic material having a first modulus of elasticity in a first direction and second modulus of elasticity in a second direction. The first modulus of elasticity is smaller than the second modulus of elasticity so that the body is configured to collapse in the first direction and resist compression in the second direction. The manifold portion surrounds the compression portion and is configured to provide negative pressure and/or add or remove fluids. The negative pressure source is configured to provide negative pressure to at least the compression portion. The negative pressure collapses the body in the first direction, thereby generating a compressive force in the first direction.

In some embodiments, the first direction is a substantially lateral direction and the second direction is a substantially vertical direction.

In some embodiments, the wound therapy system further includes fabric strips configured to secure the wound dressing to an abdominal wall. The fabric strips can be formed of a compressive material. The fabric strips are configured to transfer the lateral compressive force to the abdominal wall.

In some embodiments, the compression portion defines a longitudinal axis and includes a pattern of voids configured to collapse in the lateral direction under the negative pressure, thereby exerting the lateral compressive force towards the longitudinal axis.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE FIGURES

FIG. 6 is a front view of a compressive layer of a wound dressing of the wound therapy system of FIG. 1 according to some embodiments.

FIG. 7 is a section view of the compressive layer taken along the lines 7-7 of FIG. 6.

FIG. 11 is a front view of a compressive layer of a wound dressing of the wound therapy system of FIG. 1 according to some embodiments.

FIG. 12 is a front view of a compressive layer of a wound dressing of the wound therapy system of FIG. 1 according to some embodiments.

FIG. 18 is a front view of a compressive layer of a wound dressing of the wound therapy system of FIG. 1 according to some embodiments.

FIG. 19 is a front view of a compressive layer of a wound dressing of the wound therapy system of FIG. 1 according to some embodiments.

FIGS. 22A-22C are a schematic representation of a felting process according to some embodiments.

FIGS. 23A and 23B illustrate a compressive layer formed of a felted material according to some embodiments.

DETAILED DESCRIPTION

Overview

Figure 1:
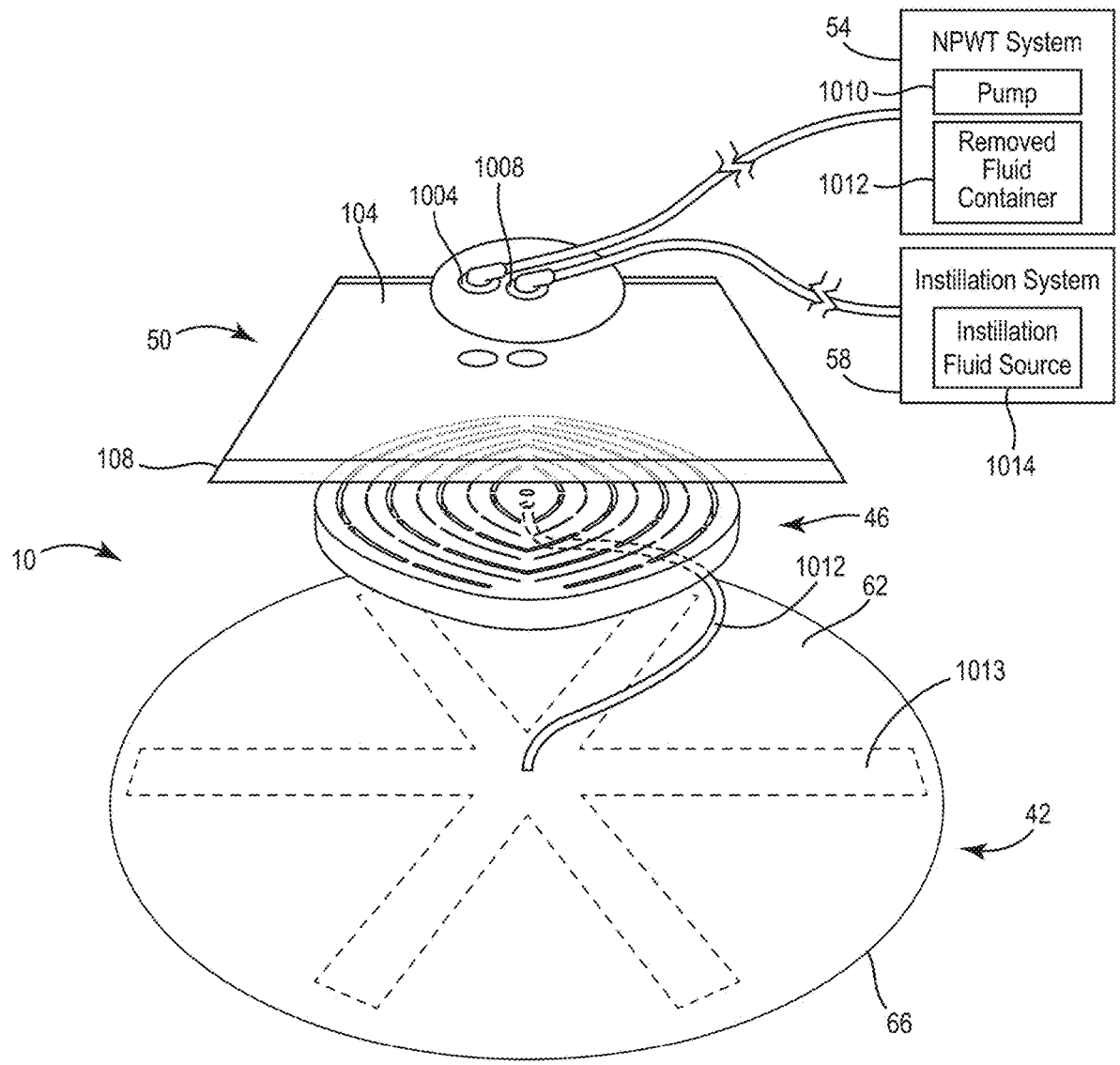
FIG. 1 is an exploded view of a wound therapy system for a deep abdominal wound.

Referring generally to the FIGURES, a wound therapy system for treating a deep abdominal wound and/or an open abdomen is shown, according to various embodiments. The phrase "deep abdominal wound" refers to an abdominal incision that includes an incision in the fascial layer to access the abdominal cavity. The fascial layer is a layer of tissue that surrounds and supports the abdominal contents (e.g., the bowels and the internal organs). The phrase "open abdomen" refers to conditions in which a deep abdominal wound is left open (e.g., the abdominal incision is not resealed) for a period of time. For example, the abdomen may be left open to accommodate swelling of the bowels and/or other abdominal contents (e.g., internal organs). The abdomen may also be left open in conditions in which further surgery in the abdominal cavity is required. More specifically, the wound therapy system is for treating open abdominal incisions that include an incision in the fascial layer. The wound therapy system is configured to engage the fascial layer proximate the fascial incision and rejoin the cut ends of the fascial layer, preventing retraction of the cut ends fascial later during the open abdomen conditions.

The wound therapy system includes a plurality of layers, including a visceral protective layer, a compressive layer, and a sealing layer. The wound therapy system can be used with a negative pressure wound therapy (NPWT) system and/or an installation system. The visceral protective layer is positioned within the abdominal cavity and wrapped around the bowels and internal organs. The compressive layer is positioned within the abdominal cavity and is configured to contract laterally and/or radially under negative pressure to pull the cut ends of the fascial layer together. The sealing layer is configured to be affixed to a patient's skin surrounding an abdominal incision and to provide a sealed space (e.g., in the open abdomen).

More specifically, the compressive layer is configured to overlie a fascial incision formed proximate a bottom of the abdominal incision. The compressive layer has a generally elliptical shape to conform to a shape of the open abdominal incision. The compressive layer 46 can be made from a porous and permeable foam-like material and can be adapted to wick fluid (e.g. exudate) from the wound and can include in-molded manifold structures for distributing negative pressure throughout the wound dressing during NPWT treatments. The compressive layer can be configured to first collapse in a generally lateral and/or radially inward direction and then collapse in a generally vertical direction under negative pressure. The compressive layer can be made from an isotropic material that has been treated to generate anisotropic material properties. More specifically, the anisotropic material properties have been generated by cutting a pattern of voids into the compressive layer material such that the compressive layer material compresses more along a lateral axis than along a vertical axis and/or a longitudinal axis to exert a generally lateral and/or radially inward distributed force on the cut ends of the fascia to draw the cut ends of the fascia together.

Additional features and advantages of the wound therapy system are described in detail below.

Wound Therapy System

Figure 2:
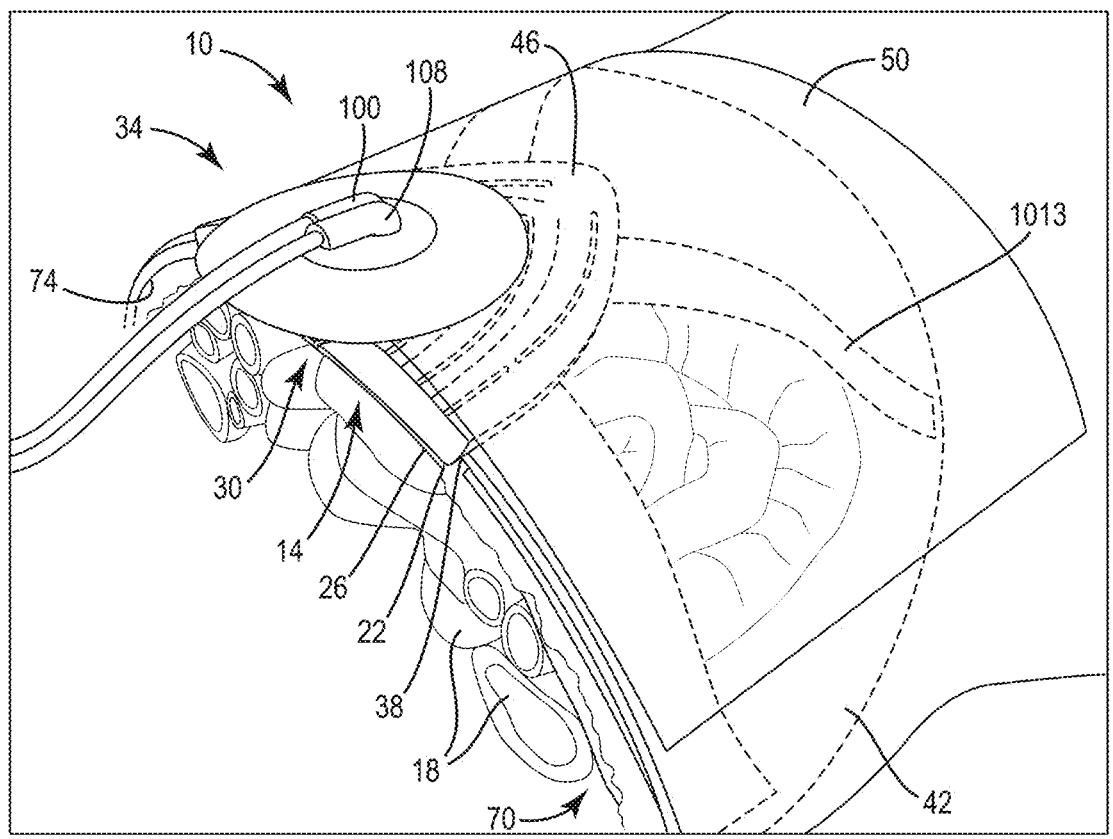
FIG. 2 is a cross-sectional view of the wound therapy system deployed in an abdomen.

Referring to FIGS. 1-2, a wound therapy system 10 is shown, according to an exemplary embodiment. FIG. 1 is an exploded view of the wound therapy system 10. FIG. 2 is a cross-sectional view of the wound therapy system 10 engaged with a treatment site 14 of a patient. In the illustrated embodiment, the treatment site 14 is a body cavity, such as an abdominal cavity. The treatment site 14 may include the abdominal contents 18 or tissue that is proximate the abdominal cavity 14. The abdominal contents 18 may include the fascia 26 and/or the internal organs.

In various embodiments, the wound therapy system 10 can be used to treat a deep abdominal incision 22. The term "deep abdominal incision" is used generally herein to refer to an abdominal incision 22 that penetrates a fascia 26 of a patient. The deep abdominal incision 22 is a substantially straight incision. In the illustrated embodiment, the deep abdominal incision 22 is shown as a generally vertical incision. However, the wound therapy system 10 can be used to treat other orientations of substantially straight incisions (e.g. substantially horizontal incisions, substantially diagonal incisions).

More specifically, and with reference to FIG. 2, the wound therapy system 10 can be used to treat an "open abdomen" condition, in which a deep abdominal wound 22 is left open for a period of time. When in the "open abdomen" condition, the edges of the incision splay apart in a substantially lateral direction 34, yielding an substantially elliptical-shaped opening 38 in the abdomen. The wound therapy system 10 is shown to include a plurality of layers, including a visceral protective layer 42, a compressive layer 46, and a sealing layer 50. The wound therapy system 10 can be used with a negative pressure wound therapy (NPWT) system 54 and/or an instillation system 58.

The Visceral Protective Layer

Referring to FIG. 1, the visceral protective layer 42 is shown to include a first surface 62 and a second, fascia-facing surface 66 opposite the first surface 62. The visceral protective layer 42 is positioned within a patient's abdominal cavity. When the visceral protective layer 42 is applied to the wound, the first surface 62 faces away from the fascia, whereas the second surface 66 faces toward the fascia. In some embodiments, the first surface 62 of the visceral protective layer 42 contacts the compressive layer 46. In some embodiments, the second surface 66 of the visceral protective layer 42 contacts the abdominal contents 18. The visceral protective layer 42 is flexible and wraps about the abdominal contents 18 and may extend into a first paracolic gutter 70 (FIG. 2) and a second paracolic gutter 74 (FIG. 2). The first paracolic gutter 70 and the second paracolic gutter 74 may each be an open space on opposing sides of the abdominal cavity 14 and among the abdominal contents 18.

The visceral protective layer 42 can made of a material that is fluid-impermeable and intended to not irritate the patient's fascia and internal organs. For example, in some embodiments, the visceral protective layer 42 can be made of a polyurethane film. As described in greater detail below, in such an embodiment, the visceral protective layer 42 may encapsulate the instillation system 58 and include a plurality of fenestrations for distribution of instillation fluid.

The Compressive Layer

Referring now to FIGS. 3-21, exemplary embodiments of compressive layers for use with the wound therapy system are shown. The compressive layer is shaped to be positioned within at least a portion of the abdominal incision 22, such as an incision formed as part of a vertical laparotomy. The compressive layer is configured to overlie a fascial incision formed proximate a bottom of the abdominal incision 22. Accordingly, the compressive layer is shaped to conform to a shape of the open abdominal incision 22. For example, as shown in FIGS. 3-21, the compressive layer has a generally elliptical shape.

Figures 3, 4:
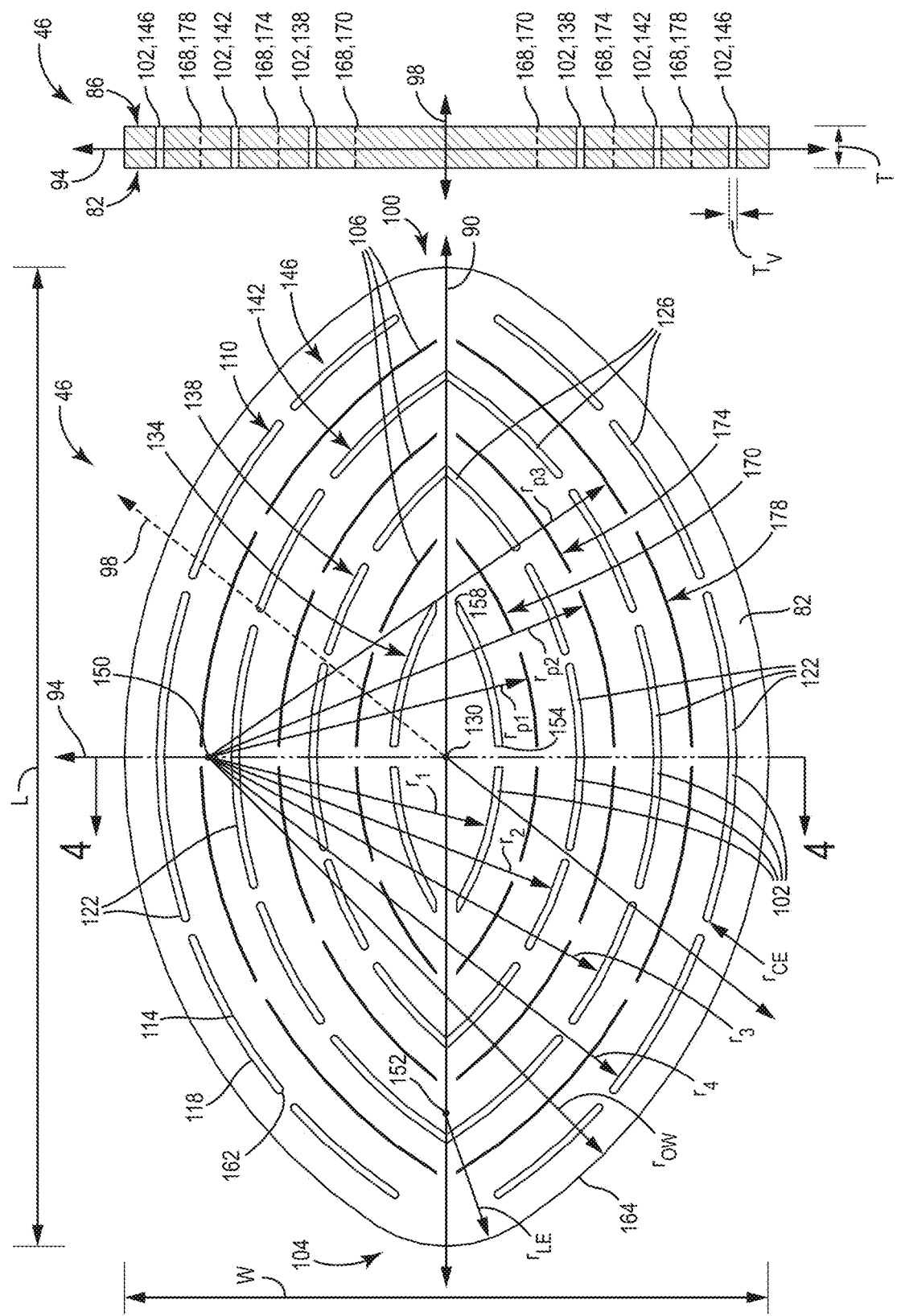
FIG. 3 is a front view of a compressive layer of a wound dressing of the wound therapy system of FIG. 1 according to some embodiments.
FIG. 4 is a section view of the compressive layer taken along the lines 4-4 of FIG. 3.
Figure 5:
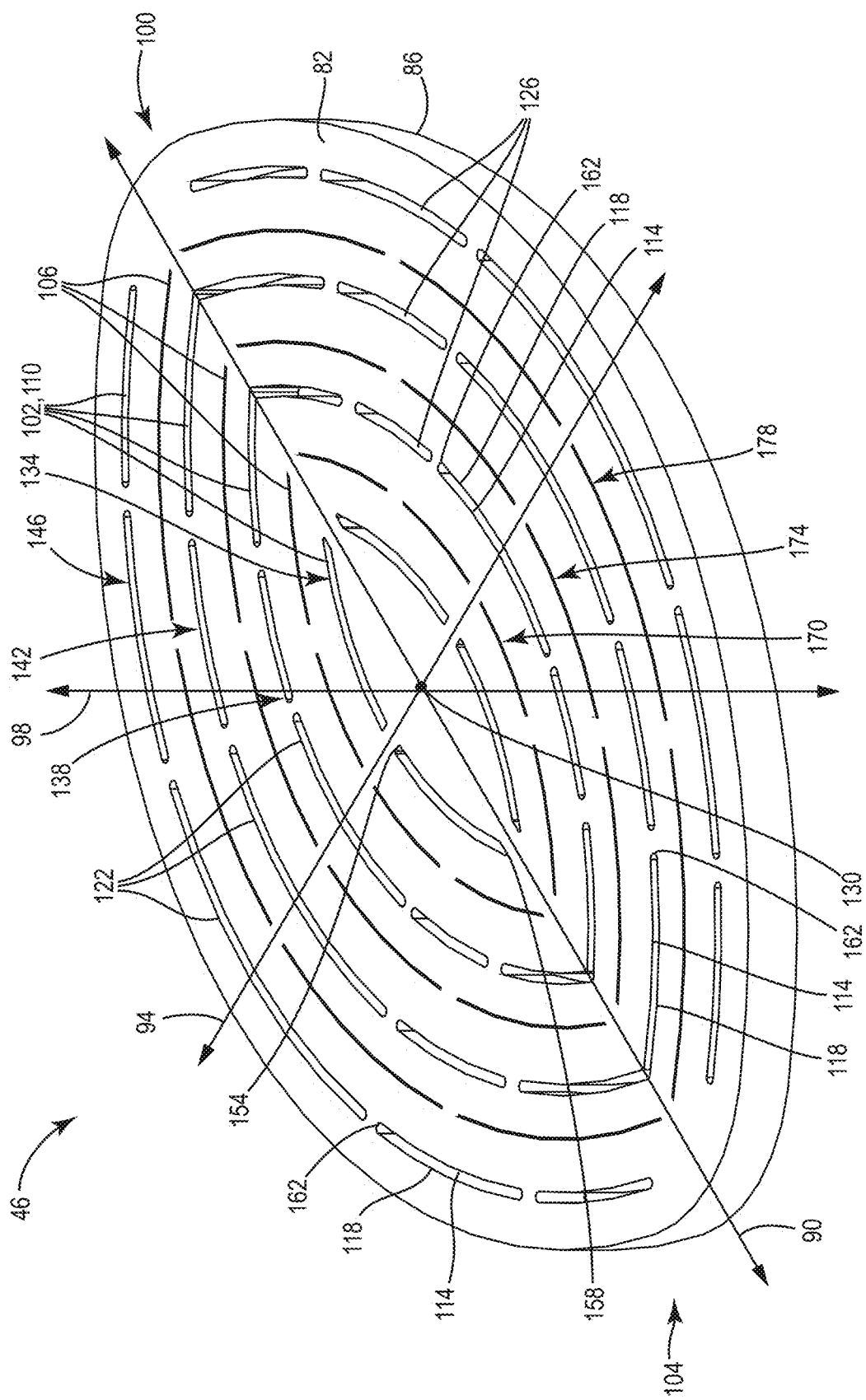
FIG. 5 is a perspective view of the compressive layer of FIG. 3.

Referring now to FIGS. 3-5, a compressive layer 46 is shown, according to an exemplary embodiment. FIG. 3 is a front view of the compressive layer 46. FIG. 4 is a section view of the compressive layer of FIG. 3 taken along lines 4-4 of FIG. 3. FIG. 5 is a perspective view of the compressive layer 46 of FIG. 3. The compressive layer 46 is configured to overlie a fascial incision, such as an incision formed as part of a vertical laparotomy.

The compressive layer 46 is shown to include a first surface 82 and a second, fascia-facing, surface opposite the first surface 82. When the compressive layer 46 is applied to a wound, the first surface 82 faces away from the fascia and the second surface faces toward the fascia 26. In some embodiments, the second surface 86 of the compressive layer 46 contacts the first surface 82 of the visceral protective layer 42. In some embodiments, the first surface of the compressive layer 46 contacts the sealing layer 50. The compressive layer 46 is shaped to conform to a shape of the open abdominal incision 22 so that the compressive layer 46 is configured to be positioned within the open abdominal incision 22. When in the "open abdomen" condition, the edges of the incision splay apart in a substantially lateral direction 34, yielding an substantially elliptical-shaped opening 38 in the abdomen. Accordingly, as shown in FIGS. 3 and 5, the compressive layer 46 has a generally elliptical shape. The compressive layer 46 includes a longitudinal axis 90 defining a longitudinal direction, a lateral axis 94 defining a lateral direction, and a vertical axis 98 defining a vertical direction. The compressive layer 46 includes a first tapered end 100 and a second tapered end 104. The first tapered end 100 and the second tapered end 104 are spaced part along the longitudinal axis 90.

The compressive layer 46 can be made from a porous and permeable foam-like material. More particularly, the compressive layer 46 can be made from a reticulated, open-cell polyester polyurethane or polyether polyurethane foam that allows good permeability of wound fluids while under a reduced pressure. One such foam material that has been used is the VAC® Granufoam® material that is available from Kinetic Concepts, Inc. (KCI) of San Antonio, Tex. Any material or combination of materials might be used for the compressive layer provided that the compressive layer is operable to distribute the reduced pressure and provide a distributed compressive force along the wound site. The compressive layer 46 adapted to wick fluid (e.g. exudate) from the wound and can include in-molded manifold structures for distributing negative pressure throughout the wound dressing 10 during NPWT treatments.

The density of the compressive layer material, e.g., Granufoam® material, is typically in the range of about 1.3 lb/ft$^3$-1.6 lb/ft$^3$ (20.8 kg/m$^3$-25.6 kg/m$^3$). The reticulated pores of the Granufoam® material generally range in size between about 400 to 600 microns, but other materials with other pore sizes may be used. A concentration of the reticulated pores generally ranges between 40-50 pores per inch, although other concentrations of pores can be used.

An applied force, such as a suction force generated by a negative pressure source of the NPWT system 54, can cause the collapse of the pores and contraction of the compressive layer 46. The tendency of the compressive layer 46 to compress under an applied force is based on the modulus of elasticity of the compressive layer material. Compressive layer materials with a relatively low modulus of elasticity undergo more compression under an applied force, but are also prone to buckling and deformation. Compressive layer materials with a relatively high modulus of elasticity undergo less compression under an applied force, but are also less prone to buckling and deformation.

The modulus of elasticity of the compressive layer material can be based on a concentration of the pores, an orientation of the pores, or a combination of the size, concentration, and orientation of the pores. In some embodiments, the pores may be shaped and/or oriented so that the modulus of elasticity of the compressive layer material is isotropic (e.g. the compression occurs generally evenly in along the longitudinal axis 90, the lateral axis 94, and the vertical axis 98). When the modulus of elasticity is isotropic, the contraction of the compressive layer material in the longitudinal direction, the lateral direction, and the vertical direction is the same under negative pressure. In such an embodiment, the pores may have a shape that is similar along the longitudinal axis 90, the lateral axis 94, and the vertical axis 98 (e.g. spherical, etc.) or the pores may have asymmetric shapes but may be randomly oriented throughout the compressive layer material, such that the net compressive layer material has the same effective orientation pores along the longitudinal axis 90, the lateral axis 94, and the vertical axis 98. In other embodiments, the pores may be oriented so that modulus of elasticity of the compressive layer material is anisotropic (e.g., the compressive layer material has different moduli of elasticity in the lateral direction, the longitudinal direction, and/or the vertical direction). In anisotropic compressive layer materials, the compressive layer material experiences different amounts of contraction in at least one of the lateral direction, the longitudinal direction, and/or the vertical direction when subjected to negative pressure. For example, the compressive layer material can be a reticulated foam that undergoes a felting process to introduce anisotropy into the reticulated foam. An exemplary felting process is described in greater detail below. In such embodiments, the pores may be elongate and oriented along the a first axis (e.g., the vertical axis 98), which can result in more compression in a second axis generally perpendicular to the first axis (e.g., the lateral axis 94).

In some embodiments, the compressive layer material can have a minimum tensile strength of approximately 10 lb/ft$^2$. In some embodiments, the compressive layer material can have a minimum elongation under tension of 110%. In some embodiments, the compressive layer material can have a minimum 25% load deflection of approximately 0.35 lb/in$^2$. In some embodiments, the compressive layer material can have a minimum 65% compression load deflection of approximately 0.43 lb/in$^2$. In some embodiments, the compressive layer material can have a minimum tear strength of 2.5 lb/in.

A compressive layer material with a higher density than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used.

In some embodiments, the compressive layer material can be a flexible rubber or rubber-like material such as natural rubber (latex), silicone, or thermoplastic elastomer (TPE). In some instances it may be desirable to add ionic silver to the foam in a microbonding process or to add other substances to the absorbent layer material such as antimicrobial agents.

In some embodiments, the compressive layer material is an isotropic material that has been treated to generate anisotropic material properties. More specifically, the anisotropic material properties have been generated by cutting a pattern of voids into the compressive layer material such that the compressive layer material compresses more along the lateral axis 94 than along the vertical axis 98 and the longitudinal axis 90. In some embodiments, the pattern of voids is cut into the compressive layer material by processes such as laser-cutting or die cutting. In other embodiments, the pattern of voids is formed in the compressive layer material by processes such as 3-D printing or molding. The shape of the voids and/or the orientation of the voids in the pattern of voids can increase a lateral strain of the compressive layer material with respect to the compressive layer material that does not include the voids. The lateral strain of the compressive layer material is a measure of the compressive layer material's tendency to undergo lateral deformation under an applied force and is given by the formula $\varepsilon = L/\Delta L$, where $\varepsilon$ is the strain of the compressive layer material, $\Delta L$ is the change of length under the applied force and L is the undeformed length of the compressive layer material. The compression of the uncut compressive layer material is governed by the compression of the pores, and is therefore a function of the size and distribution of the pores. When the compressive layer material includes a pattern of voids, the compression of the compressive layer material is governed by compression of the voids and compression of the pores. However, since the voids are approximately 3 orders of magnitude larger than the pores, the compression of the compressive layer material is mostly based on the compression of the voids.

The pattern of voids can be shaped and/or oriented to induce greater lateral deflection under pressure, which increases lateral strain. As is described in greater detail below, the design of the pattern of voids is based on the material properties of the compressive layer material. Compressive layer materials that have a relatively low modulus of elasticity (e.g. are easy to compress) include reinforcement in the middle and outer edges to prevent excessive vertical collapse. Such materials also include patterns of voids that have thicker walls around the voids to mitigate buckling. Compressive layer materials that have a relatively high modulus of elasticity do not require reinforcement in the middle or at the outer edges. Such compressive layer materials have small, thin-walled patterns of voids.

The compressive force that may be generated for a given reduced pressure is based on the stiffness of the compressive layer material and the dimensions and/or the pattern of the voids cut into the compressive layer material. For example, compression of a relatively stiff uncut compressive layer material generates smaller compressive forces than a less stiff uncut compressive layer material. However, the relatively stiff compressive layer material including a pattern of voids can generate larger compressive forces than the less stiff compressive layer material including a pattern of voids. This is because the compressive force that can be generated in a compressive layer increases with a volume of material removed from the compressive layer to form a pattern of voids. Stiffer materials can tolerate a larger amount of removed material (e.g., more voids and/or voids positioned closer together) than less stiff materials.

In some embodiments, different patterns of voids can be cut into different parts of the compressive layer material. For example, in some embodiments, the compressive layer material can include a pattern of voids configured to generate radial inward collapse of the compressive layer 46 under negative pressure. The phrases "radially inward" and "radially inward direction" are used herein to refer to movement towards a center of the compressive layer 46 in the lateral direction defined by the lateral axis 94 and the longitudinal direction defined by the longitudinal axis 90. In some embodiments, the radial inward collapse can be greater in the lateral direction than the vertical direction. In such embodiments, the pattern of voids applies a radial force on an intact portion of the fascia 26 proximate the cut ends of the fascial incision 30 and pull the intact portion of the fascial layer 26 and the cut ends of the fascial incision 30 towards each other to facilitate closure of the fascial incision 30. In other embodiments, the compressive layer material can include a pattern of voids configured to generate lateral compression of the compressive layer 46 under negative pressure. In such embodiments, the pattern of voids applies a lateral force on an intact portion of the fascia 26 and the cut ends of the fascial incision 30 pull the cut ends of the fascial incision 30 together to facilitate closure of the fascial incision 30. In other embodiments, the compressive layer material can have a first pattern of voids proximate a center of the compressive layer material for facilitating compression along the lateral axis. The lateral compression along the lateral axis draws the cut ends of the fascial incision 30 inward towards the longitudinal axis 90, reducing a distance between the cut ends of the fascial incision 30. The compressive layer material can have a second pattern of voids surrounding the first pattern of voids for facilitating radially inward (e.g. towards a center of the compressive layer material) compression of the compressive layer material. In such embodiments, the second pattern of voids applies a radial force on an intact portion of the fascia 25 proximate the cut ends of the fascial incision 30 and orient the portion of the fascial layer 26 proximate the fascial incision 30 to facilitate closure of the fascial incision 30. For example, the compressive layer 46 is positioned within the abdominal incision 22 and oriented so that the fascial incision 26 is generally aligned with the longitudinal axis 90 of the compressive layer 46. Accordingly, an inner portion of the compressive layer 46 is positioned above the fascial incision and an outer portion (e.g., proximate a perimeter of the compressive layer 46) of the compressive layer 46 is positioned over an intact portion of the fascia. Accordingly, radially inward compression of the outer portion of the compressive layer 46 pulls the intact portion of the fascial radially inward in all directions, which pulls the fascial tissue towards the area of the lateral incision.

Although the compressive layer material is discussed in the context of the compressive layer 46, the aforementioned description of the compressive layer material is also applicable to the compressive layers 186, 246, 298, 478, 364, 422, 550, 666, 738, 794, 874, and 948 of FIGS. 6-21.

Referring again to FIGS. 3-5, the compressive layer 46 has a width W in the generally lateral direction. In the illustrated embodiment, the width W is approximately 250 mm. In other embodiments, the width W can be approximately 247 mm-approximately 253 mm. In some embodiment, with W can be approximately 200 mm-300 mm. The compressive layer 46 has a length L in the generally longitudinal direction. The term "approximately" may be substituted with "within a percentage of" what is specified, where the percentage includes 0, 1, 4, and 10 percent. In the illustrated embodiment, the length L is approximately 380 mm. In other embodiments, the length L can be approximately 377 mm-approximately 383 mm. The compressive layer 46 has a thickness T in the generally vertical direction. In the illustrated embodiment, the thickness T is approximately 16 mm. In other embodiments, the thickness T can be approximately 14 mm-approximately 18 mm. In the illustrated embodiment, the compressive layer 46 can be made of the reticulated polyurethane foam (e.g., Granufoam®) material described above.

As illustrated in FIGS. 3 and 5, the compressive layer 46 includes a pattern of voids 102 and a pattern of perforations 106. The pattern of voids 102 is formed by a plurality of voids 110 (e.g., through holes) extending between the first surface 82 and the second surface 86. As shown in FIG. 3, the plurality of voids 110 of the pattern of voids 102 are oriented so that the plurality of voids 110 open in a direction that is generally parallel to the vertical axis 98. Accordingly, in the illustrated embodiment, the compression in the vertical direction is based on the pores and not the plurality of voids 110. The plurality of voids 110 are generally elongate and curved. As shown in FIG. 4, the plurality of voids 110 have a thickness $T_V$ of approximately 3 mm. The plurality of voids 110 include a concave surface 114 and a convex surface 118. The plurality of voids 110 are oriented in the pattern of voids 110 so that the convex surfaces 118 of the plurality of voids 110 follows a curved contour of the compressive layer 46. The plurality of voids 110 are oriented so that the concave surfaces 114 are facing the longitudinal axis 90. Accordingly, in the presence of negative pressure, the plurality of voids 110 are configured to collapse towards the longitudinal axis 90. More specifically, a first portion 122 of the plurality of voids 110 is generally parallel to the longitudinal axis 90 and is configured to collapse laterally towards (e.g. perpendicularly with respect to) the longitudinal axis 90. A second portion 126 of the plurality of voids 110 is angled with respect to the longitudinal axis 90 and is configured to collapse radially inward (e.g., towards a center 130 of the compressive layer) towards the longitudinal axis 90. As shown in FIG. 3, the plurality of voids 110 of the pattern of voids are oriented along the longitudinal axis 90 and the lateral axis 94. Accordingly, in the illustrated embodiment, the compression in the lateral and longitudinal direction is based on the position and/or the orientation of the plurality of voids 110. The plurality of voids 110 are positioned so that most of the thickness of the plurality of voids 110 generally extends along the lateral axis 94, so the plurality of voids 110 generate the most compression generally along the lateral axis 94. The pattern of voids 110 is symmetric about the lateral axis 94 and the longitudinal axis 90. Accordingly, compression in the lateral and the longitudinal directions is symmetric about the lateral axis 94 and the longitudinal axis 90, respectively.

With continued reference to FIG. 3, the pattern of voids 102 includes a first ring of voids 134, a second ring of voids 138, a third ring of voids 142, and a fourth ring of voids 146. The position of the first ring of voids 134, the second ring of voids 138, the third ring of voids 142, and the fourth ring of voids 146 is described with respect to a reference point 150 that is offset approximately 93 mm from the center 130 of the compressive layer 46 along the lateral axis 94. In some embodiments, the reference point may be offset approximately 90 mm-96 mm from the center 130 of the compressive layer 46. The first ring of voids 134 surrounds the center of the compressive layer 46. A radius of curvature $r_1$ between the first ring of voids 134 and the reference point 150 is approximately 112 mm. In some embodiments, the radius of curvature $r_1$ can be between approximately 109 mm and approximately 115 mm. A first end 154 of the plurality of voids 110 is adjacent and generally parallel to the lateral axis 94. A second end 158 of the plurality of voids 110 is adjacent and generally parallel to the longitudinal axis 90. Adjacent second ends 158 of the plurality of voids 110 are spaced apart approximately 8 mm. In some embodiments, the adjacent second ends 158 may be spaced apart approximately 5 mm-approximately 11 mm. The second ring of voids 138 surrounds the first ring of voids 134. A radius of curvature $r_2$ between the second ring of voids 138 and the reference point 150 is approximately 143.5 mm. In some embodiments, the radius of curvature $r_2$ can be between approximately 140.5 mm and approximately 146.5 mm. The second ring of voids 138 includes a portion of voids 110 that are generally V-shaped and intersect the longitudinal axis 90. A portion of voids 110 extends between the generally V-shaped portion of voids 110 and is generally curved. The third ring of voids 142 surrounds the second ring of voids 138. A radius of curvature $r_3$ between the third ring of voids 142 and the reference point 150 is approximately 173.5 mm. In some embodiments, the radius of curvature $r_3$ can be between approximately 170.5 mm and approximately 176.5 mm. The third ring of voids 142 includes a portion of voids 110 that are generally V-shaped and intersect the longitudinal axis 90. A portion of voids 110 extends between the generally V-shaped portion of voids 110 and is generally curved. The fourth ring of voids 146 surrounds the third ring of voids 142 and includes voids 110 that are generally curved. A radius of curvature $r_4$ between the fourth ring of voids 146 and the reference point 150 is approximately 202.5 mm. In some embodiments, the radius of curvature $r_4$ can be between approximately 199.5 mm and approximately 205.5 mm. The plurality of voids 110 of the second ring of voids 138, the third ring of voids 142, and the fourth ring of voids 146 have curved ends 162 connecting the concave surface 114 and the convex surface 118. In the illustrated embodiment, a radius of curvature $r_{CE}$ of the curved ends 162 is approximately 1.5 mm. A radius of curvature $r_{ow}$ between an outer wall 164 of the compressive layer 46 and the reference point 150 is approximately 218 mm. In some embodiments, the radius of curvature $r_{OE}$ can be between approximately 215 mm and approximately 221 mm. In the illustrated embodiment, a radius of curvature $r_{LE}$ extending between the longitudinal ends 100, 104 of the compressive layer 46 and a second reference point 152 is approximately 50 mm. In some embodiments, the radius of curvature $r_{LE}$ can be between approximately 47 mm and approximately 53 mm. The second reference point 152 is offset approximately 140 mm from the center 130 of the compressive layer 46 along the longitudinal axis 90.

As shown in FIG. 2, When in the "open abdomen" condition, the edges of the incision splay apart in a substantially lateral direction 34, yielding an substantially elliptical-shaped opening 38 in the abdomen. The edges of the fascial incision 30 also splay apart in a substantially lateral direction. Accordingly, the fascial incision 30 is widest proximate the center 130 of the fascial incision 30 and narrowest proximate the ends of the fascial incision 30. Accordingly, in order to facilitate closure of the fascial incision 30, the compressive layer 46 is generally elliptical to overlie the fascial incision 30 and configured so that the width W of the compressive layer 46 is wider than the fascial incision 30 so that the compressive layer 46 overlies at least a portion of the fascial layer 26 proximate the fascial incision 30. The collapse of the compressive layer 46 generates the largest forces proximate the center 130 of the compressive layer 46 because the ends of the fascial incision 30 are the farthest apart proximate the center of the fascial incision.

With returning to FIGS. 3-5, the pattern of perforations 106 includes a plurality of perforations 166 extending between the first surface 82 and the second surface 86. The perforations 166 form the pattern of perforations 106. The pattern of perforations 106 includes a first ring of perforations 170, a second ring of perforations 174, and a third ring of perforations 178. The first ring of perforations 170, the second ring of perforations 174, and the third ring of perforations 178 generally follow a contour of the compressive layer 46. The first ring of perforations 170 is positioned between the first ring of voids 134 and the second ring of voids 138. In the illustrated embodiment, a radius of curvature $r_{p1}$ between the first ring of perforations 170 and the reference point 150 is approximately 128 mm. In some embodiments, the radius of curvature $r_{p1}$ can be between approximately 125 mm and 131 mm. The second ring of perforations 174 is positioned between the second ring of voids 138 and the third ring of voids 142. In the illustrated embodiment, a radius of curvature $r_{p2}$ between the second ring of perforations 174 and the reference point 150 is approximately 158 mm. In some embodiments, the radius of curvature $r_{p2}$ can be between 155 mm and 161 mm. The third ring of perforations 178 is positioned between the third ring of voids 142 and the fourth ring of voids. In the illustrated embodiment, a radius of curvature $r_{p3}$ between the third ring of perforations 178 and the reference point 150 can be approximately 188 mm. In some embodiments, the radius of curvature $r_{p3}$ can be between approximately 185 mm and 191 mm. The perforations 166 facilitate removal of a portion of the compressive layer 46 to adjust a size of the compressive layer 46. For example, the entire compressive layer 46 can be used to treat relatively large fascial incisions. In some embodiments, relatively large fascial incisions are fascial incisions that are approximately 200 mm long or longer. Concentric segments of the compressive layer 46 can be removed from the compressive layer 46 to treat relatively small fascial incisions. Since the perforations 166 are oriented in spaced apart, concentric rings, removing segments of the compressive layer 46 does not change the general contour of the compressive layer 46 and/or the forces exerted by the compressive layer 46. Accordingly, resizing the compressive layer 46 will not alter the symmetry of the compressive layer.

FIGS. 6-7 illustrate a compressive layer 180 according to another exemplary embodiment. FIG. 6 is a front view of the compressive layer 176. FIG. 7 is a section view of the compressive layer 176 taken along the lines 7-7 of FIG. 6. The compressive layer 176 is substantially similar to the compressive layer 46 shown in FIGS. 3-5. Accordingly, like numbers are used to indicate like parts between the compressive layers 46 and 176. The like parts are not further discussed herein with respect to the compressive layer 176 for the sake of brevity.

As illustrated in FIGS. 6 and 7, the compressive layer 46 includes the pattern of voids 102. The pattern of voids 102 is formed by the plurality of voids 110 (e.g., through holes) extending between the first surface 82 and the second surface 86. As shown in FIG. 6, the plurality of voids 110 of the pattern of voids 102 are oriented so that the plurality of voids 110 open in a direction that is generally parallel to the vertical axis 98. Accordingly, in the illustrated embodiment, the compression in the vertical direction is based on the pores and not the plurality of voids 110. The plurality of voids 110 are generally elongate and curved.

With continued reference to FIG. 6, the pattern of voids 102 includes a first ring of voids 134, a second ring of voids 138, a third ring of voids 142, and a fourth ring of voids 146. In the compressive layer 176, the plurality of perforations 102 have been replaced with the plurality of voids 110. More specifically, the plurality of voids 110 further includes a fifth ring of voids 180, a sixth ring of voids 182, and a seventh ring of voids 184. The fifth ring of voids 180 is positioned between the first ring of voids 134 and the second ring of voids 138. The fifth ring of voids 180 is positioned at the radius of curvature $r_{p1}$ from the reference point 150. The sixth ring of voids 182 is positioned between the second ring of voids 138 and the third ring of voids 142. The sixth ring of voids 180 is positioned at the radius of curvature $r_{p2}$ from the reference point 150. The seventh ring of voids 184 is positioned between the third ring of voids 142 and the fourth ring of voids 146. The seventh ring of voids 184 is positioned at the radius of curvature $r_{p3}$ from the reference point 150.

The plurality voids 110 of the fifth ring of voids 180, the sixth ring of voids 182, and the seventh ring of voids 184 are generally curved. The plurality voids 110 of the fifth ring of voids 180, the sixth ring of voids 182, and the seventh ring of voids 184 include the concave surface 114 and the convex surface 118. The concave surfaces 114 are substantially oriented towards the longitudinal axis 90. The plurality of voids 110 of the fifth ring of voids 180, the sixth ring of voids 182, and the seventh ring of voids 186 have curved ends 162 connecting the concave surface 114 and the convex surface 118. In the compressive layer 176, the plurality of voids 110 of the first ring 180 include the curved ends 162 connecting the concave surface 114 and the convex surface 118.

Figures 8, 9:
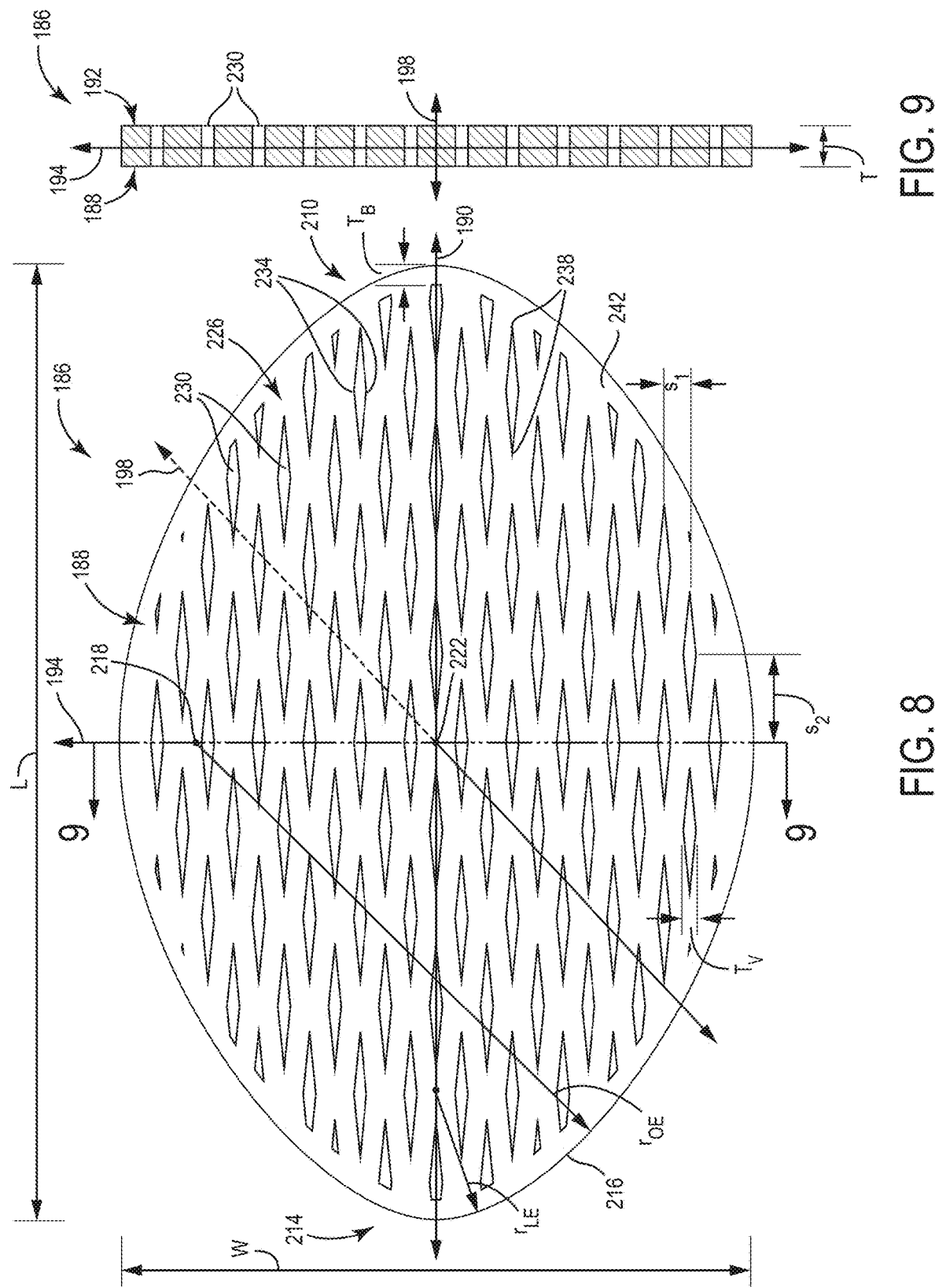
FIG. 8 is a front view of a compressive layer of the wound dressing of the wound therapy system of FIG. 1 according to another embodiment.
FIG. 9 is a section view of the compressive layer taken along the lines 7-7 of FIG. 8.
Figure 10:
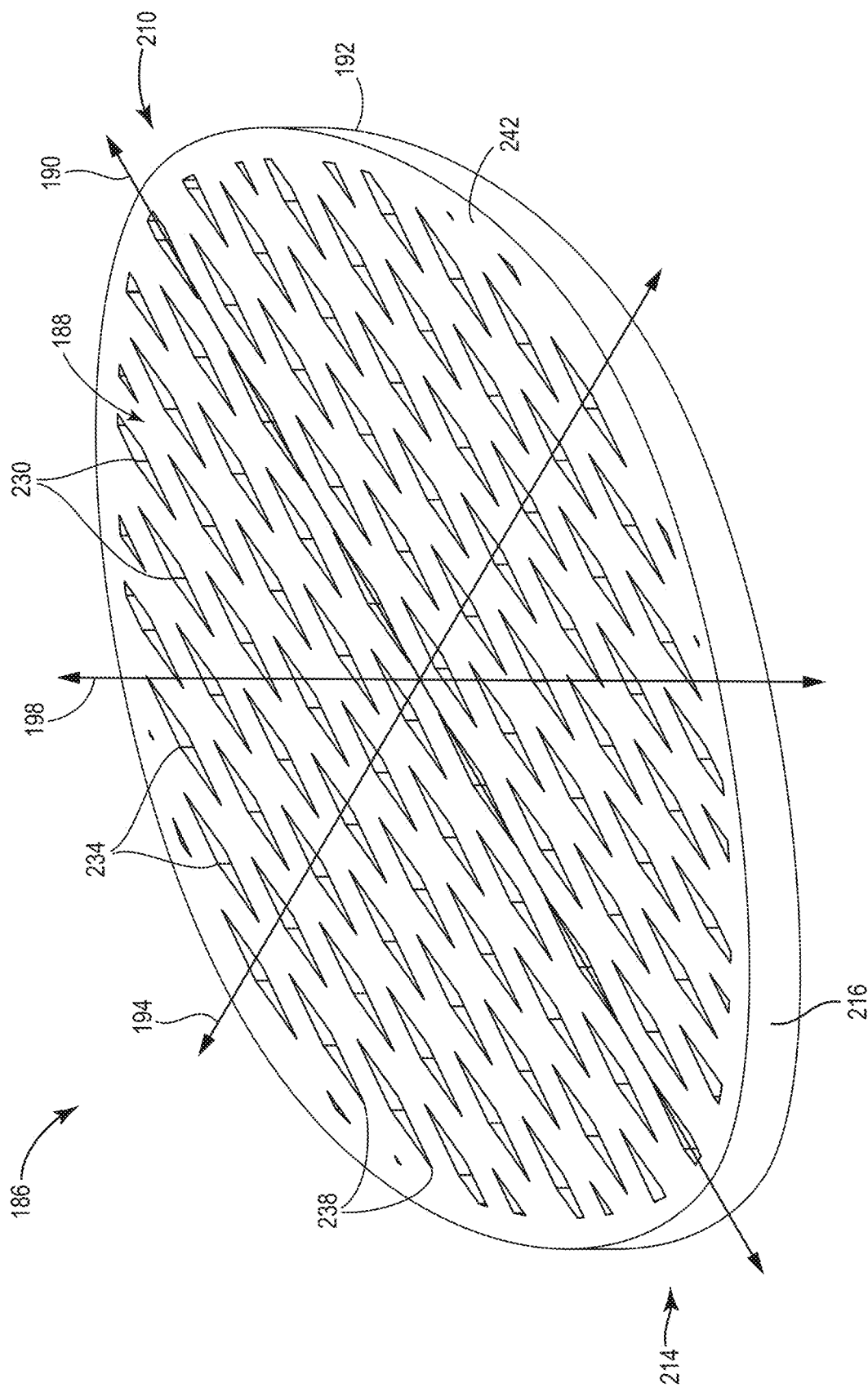
FIG. 10 is a perspective view of the compressive layer of FIG. 8.

FIGS. 8-10 illustrate a compressive layer 186 according to an another exemplary embodiment. FIG. 8 is a front view of the compressive layer 186. FIG. 9 is a section view of the compressive layer 186 taken along the lines 9-9 of FIG. 8. FIG. 10 is a perspective view of the compressive layer 186.

The compressive layer 186 is shown to include a first surface 188 and a second, fascia-facing, surface 192 opposite the first surface 188. When the compressive layer 186 is applied to a wound, the first surface 188 faces away from the fascia and the second surface faces toward the fascia 26. In some embodiments, the second surface 192 of the compressive layer 186 contacts the first surface 188 of the visceral protective layer 42. In some embodiments, the first surface of the compressive layer 186 contacts the sealing layer 50. The compressive layer 186 is shaped to conform to a shape of the open abdominal incision 22 so that the compressive layer 186 is configured to be positioned within the open abdominal incision 22. For example, as shown in FIGS. 8 and 10, the compressive layer 186 has a generally elliptical shape. The compressive layer 186 includes a longitudinal axis 190 defining a longitudinal direction, a lateral axis 194 defining a lateral direction, and a vertical axis 198 defining a vertical direction. The compressive layer 186 includes a first tapered end 210 and a second tapered end 214. The first tapered end 210 and the second tapered end 214 are spaced part along the longitudinal axis 190. In the illustrated embodiment, the compressive layer 186 can be made of the reticulated polyurethane foam (e.g., Granufoam®) material that has been felted to a firmness of 5. A firmness of 5 indicates that the reticulated polyurethane foam material has been compressed by a factor of 5 (e.g., has a thickness of approximately ⅕ of the original thickness).

The compressive layer 186 has a width W in the generally lateral direction. In the illustrated embodiment, the width W is approximately 250 mm. In other embodiments, the width W can be approximately 247 mm-approximately 253 mm. The compressive layer 186 has a length L in the generally longitudinal direction. In the illustrated embodiment, the length L is approximately 380 mm. In other embodiments, the length L can be approximately 377 mm-approximately 383 mm. The compressive layer 186 has a thickness T in the generally vertical direction. In the illustrated embodiment, the thickness T is approximately 16 mm. In other embodiments, the thickness T can be approximately 14 mm-approximately 18 mm. A radius of curvature $r_{OE}$ between an outer edge 216 of the compressive layer 186 and a reference point 218 is approximately 218 mm. In some embodiments, the radius of curvature $r_{OE}$ can be between approximately 215 mm and approximately 221 mm. In the illustrated embodiment, the reference point 218 is offset approximately 93 mm from a center 222 of the compressive layer 186 along the lateral axis 194. In some embodiments, the reference point can be offset approximately 90 mm-approximately 96 mm from the center 222 of the compressive layer 186 along the lateral axis 194. A radius of curvature $r_{LE}$ extending between the longitudinal ends 210, 214 of the compressive layer 186 and a second reference point 220 is approximately 50 mm. In some embodiments, the radius of curvature $r_{LE}$ can be between approximately 47 mm and approximately 53 mm. The second reference point 218 is offset approximately 140 mm from the center 222 of the compressive layer 186 along the longitudinal axis 190.

As illustrated in FIGS. 8-10, the compressive layer 186 includes a pattern of voids 226. The pattern of voids 226 is formed by a plurality of voids 230 (e.g., through holes) extending between the first surface 188 and the second surface 192. As shown in FIG. 8, the plurality of voids 230 of the pattern of voids 226 are oriented so that the plurality of voids 230 open in a direction that is generally parallel to the vertical axis 198. Accordingly, in the illustrated embodiment, the compression in the vertical direction is based on the pores. The plurality of voids 230 are generally diamond-shaped and have a pair of obtuse vertices 234 and a pair of acute vertices 238. The plurality of voids 230 have a length $L_V$ in a direction generally parallel to the longitudinal axis 190. In the illustrated embodiment, the length $L_V$ is approximately 50 mm. In some embodiments, the length $L_V$ can be between 47 mm and 53 mm. The voids have a thickness $T_V$ in a direction generally parallel to the lateral axis 194. In some embodiments, the thickness $T_V$ is approximately 5 mm. In some embodiments, the thickness $T_V$ can be between 3 mm and 10 mm. The plurality of voids 230 are positioned so that the pairs of acute vertices 238 are positioned in rows that are generally parallel to the longitudinal axis 190 and the pairs of obtuse vertices 234 are positioned in rows that are generally parallel to the lateral axis 194. In the illustrated embodiment, a spacing S1 between the acute vertices 238 of adjacent plurality of voids 230 is approximately 10 mm in a direction generally parallel to the lateral axis 194. In some embodiments, the spacing S1 can be between approximately 7 mm and approximately 10 mm. In the illustrated embodiment, a spacing S2 between obtuse vertices 234 of adjacent plurality of voids 230 is approximately 35 mm. In some embodiments, the spacing S2 can be between approximately 32 mm and approximately 38 mm. A border region 242 extends around a perimeter of the compressive layer 186. The border region 242 does not include any of the plurality of voids 230. Accordingly, the border region 242 is configured to help the compressive layer 186 maintain its shape under negative pressure conditions. In the illustrated embodiment, the border region 242 has a thickness $T_B$ of approximately 8 mm. In other embodiments, the thickness $T_B$ can be between approximately 8 mm and approximately 12 mm. In some embodiments, the thickness $T_B$ can be at least 8 mm.

As shown in FIGS. 8 and 10, the plurality of voids 230 are oriented so that the thickness T of the plurality of voids 230 is oriented along the lateral axis 194. Accordingly, in the illustrated embodiment, the compression due to the plurality of voids 230 is in the lateral direction. The pattern of voids 226 is symmetric about the lateral axis 194 and the longitudinal axis 190. Accordingly, compression in the lateral and the longitudinal directions is symmetric about the lateral axis 194 and the longitudinal axis 190, respectively. In some embodiments, the compressive layer 186 can include a plurality of perforations similar to the plurality of perforation described above with respect to FIGS. 3-5.

FIG. 11 illustrates a front view of a compressive layer 246 according to an another exemplary embodiment. The compressive layer 246 is shown to include a first surface 250 and a second, fascia-facing, surface (not shown) opposite the first surface 250. When the compressive layer 246 is applied to a wound, the first surface 250 faces away from the fascia and the second surface faces toward the fascia 26. In some embodiments, the second surface of the compressive layer 246 contacts the first surface 250 of the visceral protective layer 42. In some embodiments, the first surface of the compressive layer 246 contacts the sealing layer 50. The compressive layer 246 is shaped to conform to a shape of the open abdominal incision 22 so that the compressive layer 246 is configured to be positioned within the open abdominal incision 22. For example, as shown in FIG. 11, the compressive layer 246 has a generally elliptical shape having a first tapered end 248 and a second tapered end 252 The compressive layer 246 includes a longitudinal axis 254 defining a longitudinal direction, a lateral axis 258 defining a lateral direction, and a vertical axis 260 defining a vertical direction. The first tapered end 248 and the second tapered end 252 are substantially oriented along the longitudinal axis 254. The compressive layer 246 has similar dimensions to the compressive layers 78 and 186. For the sake of brevity, these dimensions are not further discussed herein.

As illustrated in FIG. 11, the compressive layer 246 includes a pattern of voids 262. The pattern of voids 262 is formed by a plurality of voids 266 (e.g., through holes) extending between the first surface 250 and the second surface similar to what is shown in FIGS. 4 and 9 for the compressive layers 46, 186, respectively. The plurality of voids 266 of the pattern of voids 262 are oriented so that the plurality of voids 266 open in a direction that is generally parallel to the vertical axis 260. Accordingly, in the illustrated embodiment, the compression in the vertical direction is based on the pores. The pattern of voids 262 includes a first pattern of voids 270 formed by a first plurality of voids 274 and a second pattern of voids 278 formed by a second plurality of voids 282. The first plurality of voids 274 is configured to facilitate lateral compression under negative pressure. The first plurality of voids 274 are elongate voids having lengths that are generally parallel to the longitudinal axis. The first plurality of voids 274 have a thickness T that is oriented along the lateral axis 258. Accordingly, the first plurality of voids 274 collapses in the generally lateral direction under negative pressure. The second plurality of voids 282 are concentric voids oriented about a center 286 of the compressive layer 246. The second plurality of voids 282 are configured to collapse radially inward under negative pressure.

The pattern of voids 262 includes reinforcement throughout the compressive layer 246. For example, an elongate portion 290 proximate the longitudinal axis 254 of the compressive layer 246 does not include the plurality of voids 266 to prevent excessive vertical collapse. Additionally, portions of uncut compressive layer material extending between the plurality of voids 266 form relatively thick walls 294 to prevent excessive vertical collapse. Accordingly, the pattern of voids 262 can be used with a compressive layer material having a relatively low modulus of elasticity. In some embodiments, the material with the relatively low modulus of elasticity is the Granufoam material described above, which has a 25% compressive load deflection of 0.35 lb/in$^2$ and a 65% compressive load deflection of 0.43 lb/in$^2$.

The pattern of voids 262 is symmetric about the lateral axis 258 and the longitudinal axis 254. Accordingly, compression in the lateral and the longitudinal directions is symmetric about the lateral axis 258 and the longitudinal axis 254, respectively. In some embodiments, the compressive layer 246 can include a plurality of perforations similar to the plurality of perforation described above with respect to FIGS. 3-5.

FIG. 12 illustrates a front view of a compressive layer 298 according to an another exemplary embodiment. The compressive layer 298 is shown to include a first surface 302 and a second, fascia-facing, surface (not shown) opposite the first surface 302. When the compressive layer 298 is applied to a wound, the first surface 302 faces away from the fascia 26 and the second surface faces toward the fascia 26. In some embodiments, the second surface of the compressive layer 298 contacts the first surface 62 of the visceral protective layer 42. In some embodiments, the first surface of the compressive layer 298 contacts the sealing layer 50. The compressive layer 298 is shaped to conform to a shape of the open abdominal incision 22 so that the compressive layer 298 is configured to be positioned within the open abdominal incision 22. For example, as shown in FIG. 12, the compressive layer 298 has a generally elliptical shape having a first tapered end 300 and a second tapered end 304. The compressive layer 298 includes a longitudinal axis 306 defining a longitudinal direction, a lateral axis 310 defining a lateral direction, and a vertical axis 314 defining a vertical direction. The first tapered end 300 and the second tapered end 304 are substantially oriented along the longitudinal axis. The compressive layer 298 has similar dimensions to the compressive layers 78 and 186. For the sake of brevity, these dimensions are not further discussed herein.

As illustrated in FIG. 12, the compressive layer 298 includes a pattern of voids 318. The pattern of voids 318 is formed by a plurality of voids 322 (e.g., through holes) extending between the first surface 302 and the second surface similar to what is shown in FIGS. 4 and 9 for the compressive layers 46, 186, respectively. The plurality of voids 322 are oriented so that the plurality of voids 322 open in a direction that is generally parallel to the vertical axis 314. Accordingly, in the illustrated embodiment, the compression in the vertical direction is based on the pores. More specifically, the pattern of voids 318 includes a first pattern of voids 326 formed by a first plurality of voids 330 and a second pattern of voids 334 formed by a second plurality of voids 338. In the illustrated embodiment, a plurality of slits 340 surrounds the portion of the compressive layer 298 that includes the first pattern of voids 326. The first plurality of voids 330 is configured to facilitate lateral compression under negative pressure. The first plurality of voids 330 are generally diamond-shaped and have a pair of obtuse vertices 342 and a pair of acute vertices 346. The first plurality of voids 330 are positioned so that the pairs of acute vertices 346 are positioned in rows that are generally parallel to the longitudinal axis 306 and the pairs of obtuse vertices 342 are positioned in rows that are generally parallel to the lateral axis 310. The second plurality of voids 338 surrounds the first plurality of voids 330 and is configured to facilitate radial compression under negative pressure. The second plurality of voids 338 have a generally hyperbolic shape. The second plurality of voids 338 are arranged in a first row and a second row that generally follow a contour of the compressive layer 342. A portion of second plurality of voids 338 is generally parallel to the lateral axis 310 to facilitate lateral compression. A portion of the second plurality of voids 338 is oriented so that the thickness of the second plurality of voids 338 is angled with respect to the lateral axis 310 to facilitate radial compression under negative pressure. The compressive layer material adjacent the second plurality of voids 338 forms a plurality of generally circular walls 350. The plurality of generally circular walls 350 are shaped to resist excessive vertical compression under negative pressure. For example, the plurality of generally circular walls 350 are generally wider than the second plurality of voids 338. The second pattern of voids 334 further includes a v-shaped void 356 proximate the ends 300, 304 of the compressive layer 298. The pattern of voids 318 is symmetric about the lateral axis 310 and the longitudinal axis 306. Accordingly, compression in the lateral and the longitudinal directions is symmetric about the lateral axis 310 and the longitudinal axis 306, respectively. In some embodiments, the compressive layer 298 can include a plurality of perforations similar to the plurality of perforation described above with respect to FIGS. 3-5.

Figure 13:
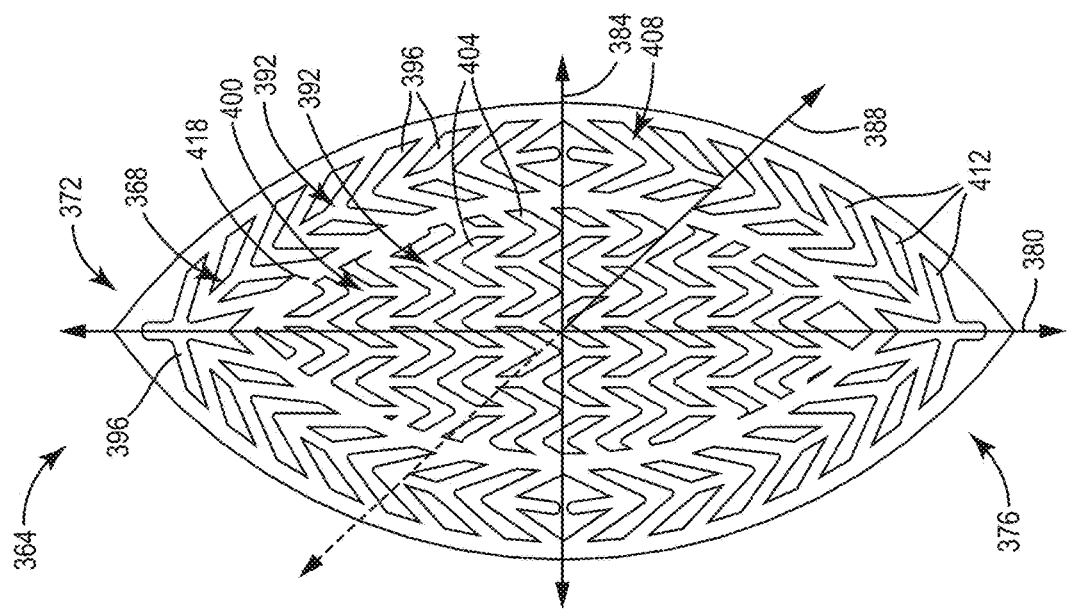
FIG. 13 is a front view of a compressive layer of a wound dressing of the wound therapy system of FIG. 1 according to some embodiments.

FIG. 13 illustrates a front view of a compressive layer 364 according to an another exemplary embodiment. The compressive layer 364 is shown to include a first surface 368 and a second, fascia-facing, surface (not shown) opposite the first surface 368. When the compressive layer 364 is applied to a wound, the first surface 368 faces away from the fascia 26 and the second surface faces toward the fascia 26. In some embodiments, the second surface of the compressive layer 364 contacts the first surface 368 of the visceral protective layer 42. In some embodiments, the first surface of the compressive layer 364 contacts the sealing layer 50. The compressive layer 364 is shaped to conform to a shape of the open abdominal incision 22 so that the compressive layer 364 is configured to be positioned within the open abdominal incision 22. For example, as shown in FIG. 13, the compressive layer 364 has a generally elliptical shape having a first tapered end 372 and a second tapered end 376. The compressive layer 364 includes a longitudinal axis 380 defining a longitudinal direction, a lateral axis 384 defining a lateral direction, and a vertical axis 388 defining a vertical direction. The first tapered end 372 and the second tapered end 374 are substantially oriented along the longitudinal axis 380. The compressive layer 364 has similar dimensions to the compressive layers 78 and 186. For the sake of brevity, these dimensions are not further discussed herein.

As illustrated in FIG. 13, the compressive layer 364 includes a pattern of voids 392. The pattern of voids 392 is formed by a plurality of voids 396 (e.g., through holes) extending between the first surface 368 and the second surface similar to what is shown in FIGS. 4 and 9 for the compressive layers 46, 186, respectively. The plurality of voids 396 are oriented so that the plurality of voids 396 open in a direction that is generally parallel to the vertical axis 388. Accordingly, in the illustrated embodiment, the compression in the vertical direction is based on the pores. More specifically, the pattern of voids 392 includes a first pattern of voids 400 formed by a first plurality of voids 404 and a second pattern of voids 408 formed by a second plurality of voids 412. The first plurality of voids 404 is configured to facilitate lateral compression under negative pressure. The first plurality of voids 404 are generally v-shaped. Adjacent voids 404 alternate between opening generally upward and opening generally downward. The first plurality of voids 404 are oriented in rows of paired upward-facing and downward-facing voids 404 that are rows are generally parallel to the lateral axis.

The second plurality of voids 412 surrounds the first plurality of voids 404 and is configured to facilitate radial compression under negative pressure. The second plurality of voids 412 are shaped like nested arrows. A first portion of the second plurality of voids 412 are positioned on a first side of the lateral axis 384 includes nested arrows pointing to the first tapered end 372 of the compressive layer 364. A second portion of the second plurality of voids 412 are positioned on a second side of the lateral axis 384 includes nested arrows pointing to the second tapered end 376 of the compressive layer 364. Under negative pressure conditions, the nested arrows of the first portion of the second plurality of voids 412 collapse into each other and towards the first tapered end 372 along a contour of a perimeter of the compressive layer 364. As indicated by the arrows, this collapse is radially inward. When the compressive layer 364 is subjected to negative pressure, the nested arrows of the second portion of the second plurality of voids 412 collapse into each other and towards the second tapered end 376 along a contour of a perimeter of the compressive layer 364. As indicated by the arrows, this collapse is radially inward. A wall 418 extends between the first pattern of voids 400 and the second pattern of voids 408 to provide support. The pattern of voids 392 is a thin-walled pattern of voids and can be used in a compressive layer material having a relatively high modulus of elasticity. The pattern of voids 392 is symmetric about the lateral axis 384 and the longitudinal axis 380. Accordingly, compression in the lateral and the longitudinal directions is symmetric about the lateral axis 384 and the longitudinal axis 380, respectively. In some embodiments, the compressive layer 364 can include a plurality of perforations similar to the plurality of perforation described above with respect to FIGS. 3-5.

Figure 14:
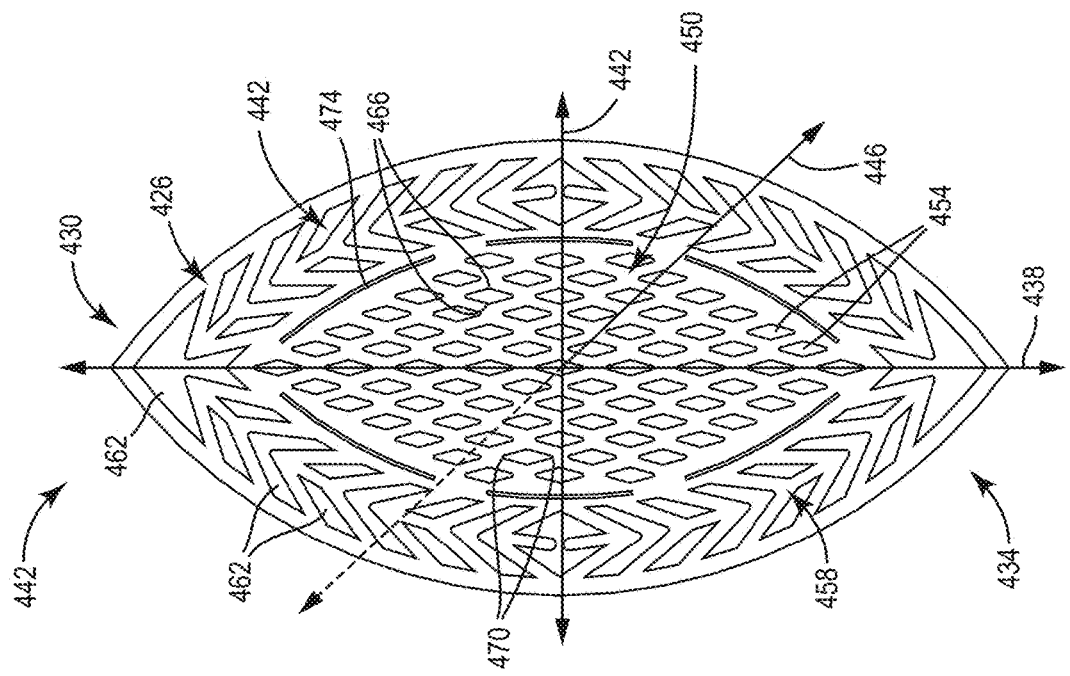
FIG. 14 is a front view of a compressive layer of a wound dressing of the wound therapy system of FIG. 1 according to some embodiments.

FIG. 14 illustrates a front view of a compressive layer 422 according to an another exemplary embodiment. The compressive layer 422 is shown to include a first surface 426 and a second, fascia-facing, surface (not shown) opposite the first surface 426. When the compressive layer 422 is applied to a wound, the first surface 426 faces away from the fascia 26 and the second surface faces toward the fascia 26. In some embodiments, the second surface of the compressive layer 422 contacts the first surface 426 of the visceral protective layer 42. In some embodiments, the first surface of the compressive layer 422 contacts the sealing layer 50. The compressive layer 422 is shaped to conform to a shape of the open abdominal incision 22 so that the compressive layer 422 is configured to be positioned within the open abdominal incision 22. For example, as shown in FIG. 14, the compressive layer 422 has a generally elliptical shape having a first tapered end 430 and a second tapered end 434. The compressive layer 422 includes a longitudinal axis 438 defining a longitudinal direction, a lateral axis 434 defining a lateral direction, and a vertical axis 446 defining a vertical direction. The first tapered end 430 and the second tapered end 434 are substantially oriented along the longitudinal axis 438. The compressive layer 422 has similar dimensions to the compressive layers 78 and 186. For the sake of brevity, these dimensions are not further discussed herein.

As illustrated in FIG. 14, the compressive layer 422 includes a pattern of voids 442. The pattern of voids 442 is formed by a plurality of voids 446 (e.g., through holes) extending between the first surface 426 and the second surface similar to what is shown in FIGS. 4 and 9 for the compressive layers 46, 186, respectively. The plurality of voids 446 of the pattern of voids 442 are oriented so that the plurality of voids 446 open in a direction that is generally parallel to the vertical axis 446. Accordingly, in the illustrated embodiment, the compression in the vertical direction is based on the pores. More specifically, the pattern of voids 442 includes a first pattern of voids 450 formed by a first plurality of voids 454 and a second pattern of voids 458 formed by a second plurality of voids 462. The first plurality of voids 454 is configured to facilitate lateral compression under negative pressure. The first plurality of voids 454 are generally diamond-shaped and have a pair of obtuse vertices 466 and a pair of acute vertices 470. The first plurality of voids 454 are positioned so that the pairs of acute vertices 470 are positioned in rows that are generally parallel to the longitudinal axis 438 and the pairs of obtuse vertices 466 are positioned in rows that are generally parallel to the lateral axis 434. The first plurality of voids 454 are positioned such that a thickness (e.g., distance between the obtuse vertices 466 of the same void 454) of each the plurality of voids 454 is generally aligned with the lateral axis 384 to facilitate compression in the lateral direction.

The second pattern of voids 458 surrounds the first pattern of voids 450 and is configured to facilitate radial compression under negative pressure. The second plurality of voids 462 are shaped like nested arrows. A first portion of the second plurality of voids 462 are positioned on a first side of the lateral axis 434 includes nested arrows pointing to the first tapered end 430 of the compressive layer 422. A second portion of the second plurality of voids 462 positioned on a second side of the lateral axis 434 includes nested arrows pointed to the second tapered end 434 of the compressive layer 422. Under negative pressure conditions, a portion of the nested arrows of the second plurality of voids 462 collapse into each other and towards the first tapered end 430 along a contour of a perimeter of the compressive layer 422. As indicated by the arrows, this collapse is radially inward.

When the compressive layer 422 is subjected to negative pressure, a portion of the nested arrows of the second plurality of voids 462 collapse into each other and towards the second tapered end 434 along a contour of a perimeter of the compressive layer 422. As indicated by the arrows, this collapse is radially inward. A plurality of slits 474 is positioned between the first pattern of voids 450 and the second pattern of voids 458. The plurality of slits 474 generally follows a contour of the perimeter of the compressive layer 422. The pattern of voids 442 is a thin-walled pattern of voids and can be used in a compressive layer material having a relatively high modulus of elasticity. For example, in some embodiments, the compressive layer 422 can be made of a reticulated foam material, such as Granufoam® that has been felted to a firmness of 5. The pattern of voids 442 is symmetric about the lateral axis 434 and the longitudinal axis 438. Accordingly, compression in the lateral and the longitudinal directions is symmetric about the lateral axis 434 and the longitudinal axis 438, respectively. In some embodiments, the compressive layer 422 can include a plurality of perforations similar to the plurality of perforation described above with respect to FIGS. 3-5.

Figure 15:
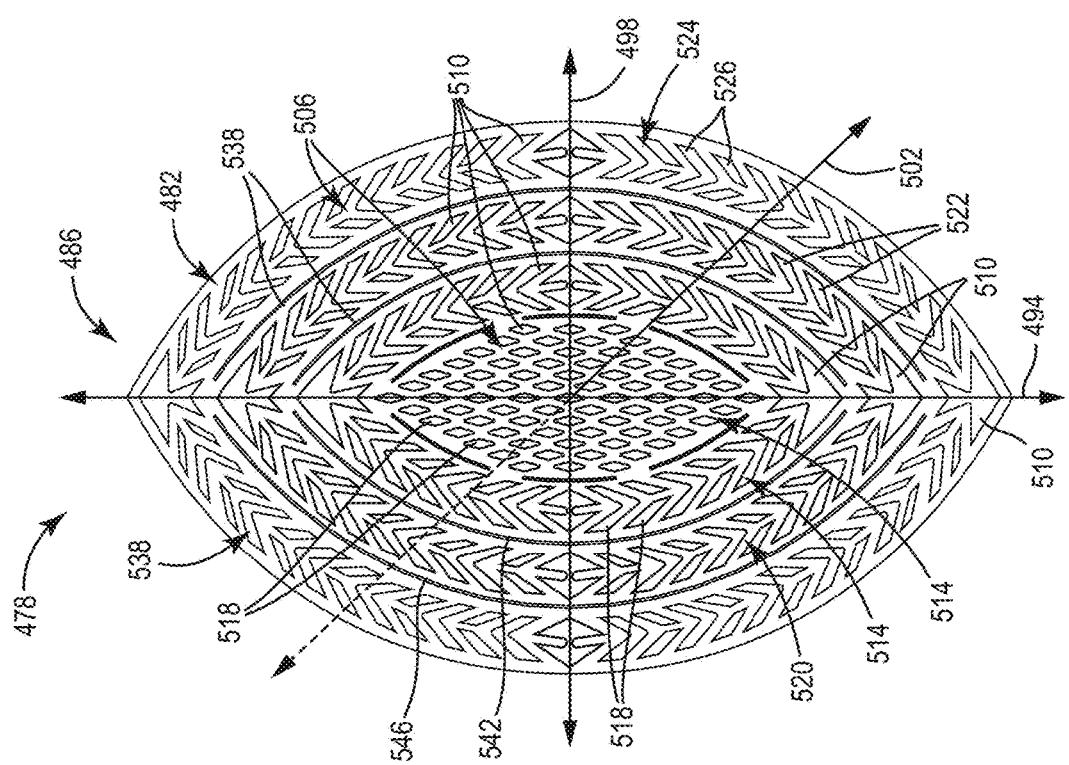
FIG. 15 is a front view of a compressive layer of a wound dressing of the wound therapy system of FIG. 1 according to some embodiments.

FIG. 15 illustrates a front view of a compressive layer 478 according to an another exemplary embodiment. The compressive layer 478 is shown to include a first surface 482 and a second, fascia-facing, surface (not shown) opposite the first surface 482. When the compressive layer 478 is applied to a wound, the first surface 482 faces away from the fascia 26 and the second surface faces toward the fascia 26. In some embodiments, the second surface of the compressive layer 478 contacts the first surface 482 of the visceral protective layer 42. In some embodiments, the first surface of the compressive layer 478 contacts the sealing layer 50. The compressive layer 478 is shaped to conform to a shape of the open abdominal incision 22 so that the compressive layer 478 is configured to be positioned within the open abdominal 221 incision. For example, as shown in FIG. 15, the compressive layer 478 has a generally elliptical shape having a first tapered end 486 and a second tapered end 490. The compressive layer 478 includes a longitudinal axis 494 defining a longitudinal direction, a lateral axis 498 defining a lateral direction, and a vertical axis 502 defining a vertical direction. The first tapered end 486 and the second tapered end 490 are substantially oriented along the longitudinal axis 494. The compressive layer 478 has similar dimensions to the compressive layers 78 and 186. For the sake of brevity, these dimensions are not further discussed herein.

As illustrated in FIG. 15, the compressive layer 478 includes a pattern of voids 506. The pattern of voids 506 is formed by a plurality of voids 510 (e.g., through holes) extending between the first surface 482 and the second surface similar to what is shown in FIGS. 4 and 9 for the compressive layers 46, 186, respectively. The plurality of voids 510 are oriented so that the plurality of voids 510 open in a direction that is generally parallel to the vertical axis 502. Accordingly, in the illustrated embodiment, the compression in the vertical direction is based on the pores. More specifically, the pattern of voids 506 includes a first pattern of voids 514 formed by a first plurality of voids 518, a second pattern of voids 520 formed by a second plurality of voids 522, a third pattern of voids 524 formed by a third plurality of voids 526, and a fourth pattern of voids 530 formed by a fourth plurality of voids 534. The first plurality of voids 518 is substantially the same as the first plurality of voids 454 discussed above with respect to FIG. 14 and is not explained in detail herein for the sake of brevity. The second plurality of voids 518 is substantially the same as the second plurality of voids 462 in FIG. 14 and is not explained in detail herein for the sake of brevity.

The third pattern of voids 522 surrounds the second pattern of voids 518 and is configured to facilitate radial compression under negative pressure. The third plurality of voids 526 are shaped like nested arrows and are oriented as described above with respect to the second plurality of voids 462 in FIG. 14 and is not explained in detail herein for the sake of brevity. The fourth pattern of voids 530 surrounds the third pattern of voids 522 and is configured to facilitate radial compression under negative pressure. The fourth plurality of voids 534 are shaped like nested arrows and are oriented as described above with respect to the second plurality of voids 462 in FIG. 14 and is not explained in detail herein for the sake of brevity. The pattern of voids 506 is a thin-walled pattern of voids 506 and can be used in a compressive layer material having a relatively high modulus of elasticity. For example, in some embodiments, the compressive layer 478 can be made of a reticulated foam material, such as Granufoam® that has been felted to a firmness of 5. The pattern of voids 406 is symmetric about the lateral axis 498 and the longitudinal axis 494. Accordingly, compression in the lateral and the longitudinal directions is symmetric about the lateral axis 498 and the longitudinal axis 494, respectively. Another example of a material having a relatively high modulus of elasticity is silicone rubber, which has a modulus of elasticity of approximately 0.14 MPa.

With continued reference to FIG. 15, the compressive layer 478 further includes a plurality of perforations 538. The plurality of perforations 538 extend between the first surface 482 and the second surface similar to what is shown in FIG. 4 with respect to the compressive layer 46. The plurality of perforations 538 are arranged in a first ring of perforations 542 and a second ring of perforations 546. The first ring of perforations 542 and the second ring of perforations 546 generally follow a contour of the compressive layer 478. The first ring of perforations 542 is positioned between the second plurality of voids 518 and the third plurality of voids 526. The second ring of perforations 546 is positioned between the third plurality of voids 526 and the fourth plurality of voids 534. The plurality of perforations 538 facilitate remelliptical of a portion of the compressive layer 478 to adjust a size of the compressive layer 478. For example, the entire compressive layer 478 can be used to treat relatively large fascial incisions. Concentric segments of the compressive layer 478 can be removed from the compressive layer 478 to treat relatively small fascial incisions. Since the plurality of perforations 538 are oriented in spaced apart, concentric rings, removing segments of the compressive layer 478 does not change the general contour of the compressive layer 478. Accordingly, resizing the compressive layer 478 does not alter the symmetry of the compressive layer 478.

Figure 16:
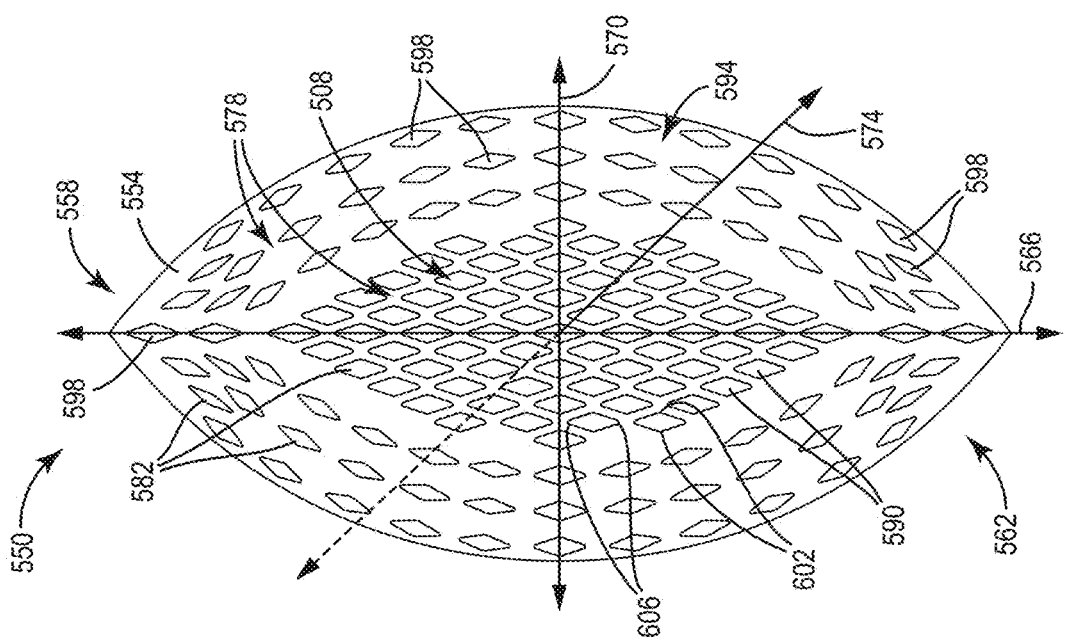
FIG. 16 is a front view of a compressive layer of a wound dressing of the wound therapy system of FIG. 1 according to some embodiments.

FIG. 16 illustrates a front view of a compressive layer 550 according to an another exemplary embodiment. The compressive layer 550 is shown to include a first surface 554 and a second, fascia-facing, surface (not shown) opposite the first surface 554. When the compressive layer 550 is applied to a wound, the first surface 554 faces away from the fascia 26 and the second surface faces toward the fascia 26. In some embodiments, the second surface of the compressive layer 550 contacts the first surface 554 of the visceral protective layer 42. In some embodiments, the first surface of the compressive layer 550 contacts the sealing layer 50. The compressive layer 550 is shaped to conform to a shape of the open abdominal incision 22 so that the compressive layer 550 is configured to be positioned within the open abdominal incision 22. For example, as shown in FIG. 16, the compressive layer 550 has a generally elliptical shape having a first tapered end 558 and a second tapered end 662. The compressive layer 550 includes a longitudinal axis 566 defining a longitudinal direction, a lateral axis 570 defining a lateral direction, and a vertical axis 574 defining a vertical direction. The first tapered end 558 and the second tapered end 662 are substantially oriented along the longitudinal axis 566. The compressive layer 550 has similar dimensions to the compressive layers 78 and 186. For the sake of brevity, these dimensions are not further discussed herein.

As illustrated in FIG. 16, the compressive layer 550 includes a pattern of voids 578. The pattern of voids 578 is formed by a plurality of voids 582 (e.g., through holes) extending between the first surface 554 and the second surface similar to what is shown in FIGS. 4 and 9 for the compressive layers 46, 186, respectively. The plurality of voids 582 are oriented so that the plurality of voids 582 open in a direction that is generally parallel to the vertical axis 574. Accordingly, in the illustrated embodiment, the compression in the vertical direction is based on the pores. More specifically, the pattern of voids 578 includes a first pattern of voids 586 formed by a first plurality of voids 590 and a second pattern of voids 594 formed by a second plurality of voids 598. The first plurality of voids 590 is configured to facilitate lateral compression under negative pressure. The first plurality of voids 590 are generally diamond-shaped and have a pair of obtuse vertices 602 and a pair of acute vertices 606. The first plurality of voids 590 are positioned so that the pairs of acute vertices 606 are positioned in rows that are generally parallel to the longitudinal axis 566 and the pairs of obtuse vertices 602 are positioned in rows that are generally parallel to the lateral axis 570. The first plurality of voids 582 are positioned such that a thickness (e.g., distance between the obtuse vertices 602 of the same void 582) of each the first plurality of voids 582 is generally aligned with the lateral axis 384 to facilitate compression in the lateral direction.

The second plurality of voids 598 surrounds the first plurality of voids 590 and is configured to facilitate radial compression under negative pressure. The second plurality of voids 598 have an diamond shape. The second plurality of voids 598 are generally oriented in three rows that generally conform to the contour of the compressive layer 550. A portion of the second plurality of voids 598 that is proximate each of the tapered ends 558, 562 are spaced close together to facilitate radian compression. A portion of the second plurality of voids 598 proximate the tapered ends 558, 562 is generally aligned with the longitudinal axis 566. The second pattern of voids 594 is a thick-walled pattern of voids and can be used in a compressive layer material having a relatively low modulus of elasticity. The pattern of voids 578 is symmetric about the lateral axis 570 and the longitudinal axis 566. Accordingly, compression in the lateral and the longitudinal directions is symmetric about the lateral axis 570 and the longitudinal axis 566, respectively. In some embodiments, the compressive layer 550 can include a plurality of perforations similar to the plurality of perforation described above with respect to FIGS. 3-5.

Figure 17:
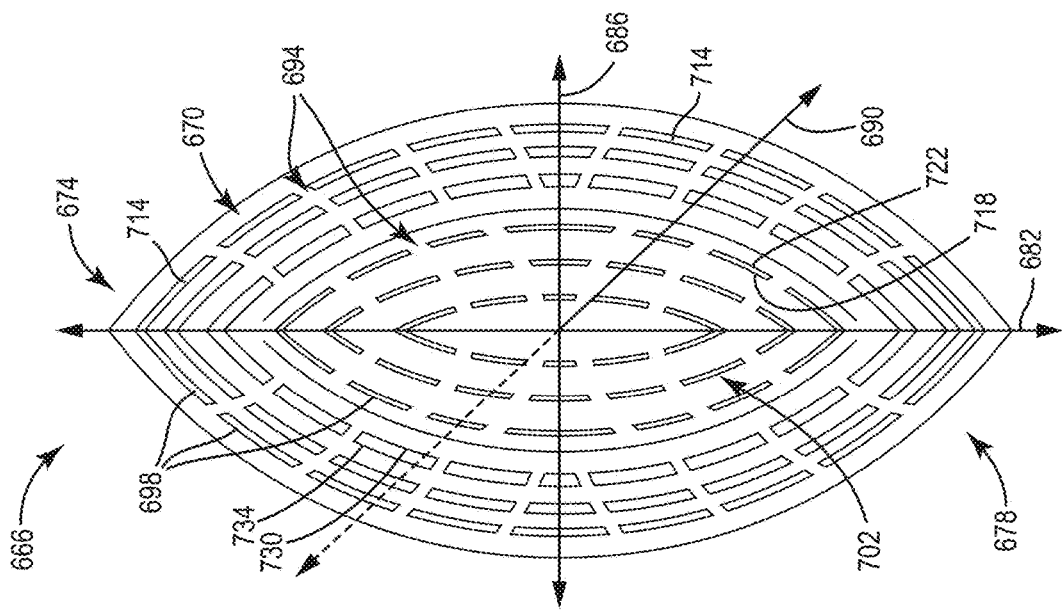
FIG. 17 is a front view of a compressive layer of a wound dressing of the wound therapy system of FIG. 1 according to some embodiments.

FIG. 17 illustrates a front view of a compressive layer 666 according to an another exemplary embodiment. The compressive layer 666 is shown to include a first surface 670 and a second, fascia-facing, surface (not shown) opposite the first surface 670. When the compressive layer 666 is applied to a wound, the first surface 670 faces away from the fascia 26 and the second surface faces toward the fascia 26. In some embodiments, the second surface of the compressive layer 666 contacts the first surface 670 of the visceral protective layer 42. In some embodiments, the first surface 670 of the compressive layer 666 contacts the sealing layer 50. The compressive layer 666 is shaped to conform to a shape of the open abdominal incision 22 so that the compressive layer 666 is configured to be positioned within the open abdominal incision 22. For example, as shown in FIG. 17, the compressive layer 666 has a generally elliptical shape having a first tapered end 674 and a second tapered end 678. The compressive layer 666 includes a longitudinal axis 682 defining a longitudinal direction, a lateral axis 686 defining a lateral direction, and a vertical axis 690 defining a vertical direction. The first tapered end 674 and the second tapered end 678 are substantially oriented along the longitudinal axis 682. The compressive layer 666 has similar dimensions to the compressive layers 78 and 186. For the sake of brevity, these dimensions are not further discussed herein.

As illustrated in FIG. 17, the compressive layer 666 includes a pattern of voids 694. The pattern of voids 694 is formed by a plurality of voids 698 (e.g., through holes) extending between the first surface 670 and the second surface similar to what is shown in FIGS. 4 and 9 for the compressive layers 46, 186, respectively. The plurality of voids 698 are oriented so that the plurality of voids 698 open in a direction that is generally parallel to the vertical axis 690. Accordingly, in the illustrated embodiment, the compression in the vertical direction is based on the pores and not by the plurality of voids 698. More specifically, the pattern of voids 694 includes a first pattern of voids 702 formed by a first plurality of voids 706 and a second pattern of voids 710 formed by a second plurality of voids 714.

The first plurality of voids 706 is configured to facilitate lateral and radial compression under negative pressure. The first plurality of voids 706 are generally elongate and curved. The first plurality of voids 706 include a concave surface 718 and a convex surface 722. The first plurality of voids 706 are oriented in the first pattern of voids 702 so that the convex surfaces 722 of the first plurality of voids 706 follows a curved contour of the compressive layer 666. The first plurality of voids 706 are oriented so that the concave surfaces 718 are facing the longitudinal axis 682. Accordingly, in the presence of negative pressure, the first plurality of voids 706 are configured to collapse towards the longitudinal axis 682. More specifically, a portion of the first plurality of voids 706 is generally parallel to the longitudinal axis 682 and is configured to collapse laterally towards (e.g. perpendicularly with respect to) the longitudinal axis 682. A portion of the first plurality of voids 706 is angled with respect to the longitudinal axis and is configured to collapse radially inward. A portion of the first plurality of voids 706 proximate each of the tapered ends 674 and 674 intersects the longitudinal axis 682. Adjacent voids 706 on opposite sides of the longitudinal axis 682 are fused to form v-shaped voids 706 that are generally aligned with the longitudinal axis 682.

The second plurality of voids 714 is configured to facilitate lateral and radial compression under negative pressure. The second plurality of voids 714 are generally elongate and curved. The second plurality of voids 714 are wider in the generally lateral direction than the first plurality of voids 706. The curved portion of the second plurality of voids 714 defines a concave surface 730 and a convex surface 734. The second plurality of voids 714 are oriented in the second pattern of voids 710 so that the convex surfaces 734 of the second plurality of voids 714 follows a curved contour of the compressive layer 666. The second plurality of voids 714 are oriented so that the concave surfaces 730 are facing the longitudinal axis 682. Accordingly, in the presence of negative pressure, the second plurality of voids 714 are configured to collapse towards the longitudinal axis 682. More specifically, a portion of the second plurality of voids 714 is generally parallel to the longitudinal axis 682 and is configured to collapse laterally towards (e.g. perpendicularly with respect to) the longitudinal axis 682. A portion of the second plurality of voids 714 is angled with respect to the longitudinal axis 682 and is configured to collapse radially inward. As shown in FIG. 17, the second plurality of voids 714 of the second pattern of voids 710 are oriented along the longitudinal axis 682 and the lateral axis 688. As indicated by the arrows, this collapse is radially inward. A portion of the second plurality of voids 714 proximate each of the tapered ends 674 and 674 intersects the longitudinal axis 682. Adjacent voids 714 on opposite sides of the longitudinal axis 682 are fused to form v-shaped voids 714 that are generally aligned with the longitudinal axis 682.

The pattern of voids 694 is a thin-walled pattern of voids and can be used in a compressive layer material having a relatively high modulus of elasticity. The pattern of voids 694 is symmetric about the lateral axis 686 and the longitudinal axis 682. Accordingly, compression in the lateral and the longitudinal directions is symmetric about the lateral axis 686 and the longitudinal axis 682, respectively. In some embodiments, the compressive layer 666 can include a plurality of perforations similar to the plurality of perforation described above with respect to FIGS. 3-5.

FIG. 18 illustrates a front view of a compressive layer 754 according to an another exemplary embodiment. The compressive layer 754 is shown to include a first surface 758 and a second, fascia-facing, surface (not shown) opposite the first surface 758. When the compressive layer 754 is applied to a wound, the first surface 758 faces away from the fascia 26 and the second surface faces toward the fascia 26. In some embodiments, the second surface of the compressive layer 754 contacts the first surface 758 of the visceral protective layer 42. In some embodiments, the first surface of the compressive layer 754 contacts the sealing layer 50. The compressive layer 754 is shaped to conform to a shape of the open abdominal incision 22 so that the compressive layer 754 is configured to be positioned within the open abdominal incision 22. For example, as shown in FIG. 18, the compressive layer 754 has a generally elliptical shape having a first tapered end 746 and a second tapered end 750. The compressive layer 754 includes a longitudinal axis 754 defining a longitudinal direction, a lateral axis 758 defining a lateral direction, and a vertical axis 758 defining a vertical direction. The first tapered end 746 and the second tapered end 750 are substantially oriented along the longitudinal axis 754. The compressive layer 754 has similar dimensions to the compressive layers 78 and 186. For the sake of brevity, these dimensions are not further discussed herein.

As illustrated in FIG. 18, the compressive layer 754 includes a pattern of voids 762. The pattern of voids 762 is formed by a plurality of voids 766 (e.g., through holes) extending between the first surface 758 and the second surface similar to what is shown in FIGS. 4 and 9 for the compressive layers 46, 186, respectively. The plurality of voids 766 are oriented so that the plurality of voids 766 open in a direction that is generally parallel to the vertical axis 758. Accordingly, in the illustrated embodiment, the compression in the vertical direction is based on the pores. More specifically, the pattern of voids 762 includes a first pattern of voids 770 formed by a first plurality of voids 774 and a second pattern of voids 778 formed by a second plurality of voids 782. The first plurality of voids 774 is configured to facilitate lateral compression under negative pressure. The first plurality of voids 774 are generally linearly-shaped and are angled towards the longitudinal axis. A majority of the thickness of the first plurality of voids 774 is oriented towards the longitudinal axis 754 to facilitate collapse of the compressive layer 754 towards the longitudinal axis 754 under negative pressure. A plurality of slits 284 extends between the first pattern of voids 770 and the second pattern of voids 778.

The second plurality of voids 782 surrounds the first plurality of voids 774 and is configured to facilitate radial compression under negative pressure. The second plurality of voids 782 includes a plurality of triangles proximate the tapered first end 746 and the tapered second end 750 and a v-shaped voids intersecting the lateral axis 758. When the compressive layer 754 is subjected to negative pressure, the triangular voids of the second plurality of voids 782 collapse radially inward and the v-shaped voids of the second plurality of voids collapses along the lateral axis 758. The remaining compressive material proximate the second plurality of voids 782 forms a wall 786. The wall 786 is shaped like a plurality of outward-facing triangles for resisting excessive vertical compression. An outer perimeter 790 of the compressive layer 738 forms a thick wall for resisting excessive vertical compression. The pattern of voids 392 is a thick-walled pattern of voids and can be used in a compressive layer material having a relatively low modulus of elasticity. The pattern of voids 770 is symmetric about the lateral axis 758 and the longitudinal axis 754. Accordingly, compression in the lateral and the longitudinal directions is symmetric about the lateral axis 758 and the longitudinal axis 754, respectively. In some embodiments, the compressive layer 754 can include a plurality of perforations similar to the plurality of perforation described above with respect to FIGS. 3-5.

FIG. 19 illustrates a front view of a compressive layer 794 according to an another exemplary embodiment. The compressive layer 794 is shown to include a first surface 798 and a second, fascia-facing, surface (not shown) opposite the first surface 798. When the compressive layer 794 is applied to a wound, the first surface 798 faces away from the fascia 26 and the second surface faces toward the fascia 26. In some embodiments, the second surface of the compressive layer 794 contacts the first surface 798 of the visceral protective layer 42. In some embodiments, the first surface of the compressive layer 794 contacts the sealing layer 50. The compressive layer 794 is shaped to conform to a shape of the open abdominal incision 22 so that the compressive layer 794 is configured to be positioned within the open abdominal incision 22. For example, as shown in FIG. 19, the compressive layer 794 has a generally elliptical shape having a first tapered end 802 and a second tapered end 806. The compressive layer 794 includes a longitudinal axis 810 defining a longitudinal direction, a lateral axis 814 defining a lateral direction, and a vertical axis 818 defining a vertical direction. The first tapered end 802 and the second tapered end 806 are substantially oriented along the longitudinal axis 810. The compressive layer 794 has similar dimensions to the compressive layers 78 and 186. For the sake of brevity, these dimensions are not further discussed herein.

As illustrated in FIG. 19, the compressive layer 794 includes a pattern of voids 822. The pattern of voids 822 is formed by a plurality of voids 826 (e.g., through holes) extending between the first surface 798 and the second surface similar to what is shown in FIGS. 4 and 9 for the compressive layers 46, 186, respectively. The plurality of voids 826 oriented so that the plurality of voids 826 open in a direction that is generally parallel to the vertical axis 818. Accordingly, in the illustrated embodiment, the compression in the vertical direction is based on the pores. More specifically, the pattern of voids 822 includes a first pattern of voids 830 formed by a first plurality of voids 834 and a second pattern of voids 838 formed by a second plurality of voids 842. The first plurality of voids 834 is configured to facilitate lateral compression under negative pressure. The first plurality of voids 834 are generally include a first portion of voids 846 that are generally linear with tapered edges and a second portion of voids 850 that have a generally X-shaped cross-section. The first plurality of voids 846 and the second plurality of voids 850 are alternately spaced. The first plurality of voids 834 are generally parallel to the longitudinal axis 810 such that the thickness of the first plurality of voids 834 extend along the lateral axis 814. Accordingly, the first plurality of voids 834 are oriented to facilitate generally lateral compression under negative pressure conditions. A plurality of slits 852 extends between the first pattern of voids 830 and the second pattern of voids 838.

The second plurality of voids 842 surrounds the first plurality of voids 834 and is configured to facilitate radial compression under negative pressure. The second plurality of voids 842 includes a first portion of voids 854 arranged in a first ring 858 and a second portion of voids 862 arranged in a second ring 866. The first ring 858 and the second ring 866 generally follow a contour of the compressive layer 794. The first ring 858 is substantially adjacent to the first pattern of voids 830. The first portion 854 and the second portion 862 of the second plurality of voids 842 are shaped like elongate arrows. The second portion of the second plurality of voids 842 are approximately twice as long as the first portion 854 of the second plurality of voids 842. The second portion 862 further includes a pair of generally elongate voids 870 spaced apart along the lateral axis 814. The thickness of the voids 870 is oriented along the lateral axis 814 to facilitate compression in the lateral direction. In the presence of negative pressure, the elongated arrows of the first portion 854 of the second plurality of voids 842 and the second portion 862 of the plurality of voids collapse into each other and towards the first tapered end 802 along a contour of a perimeter of the compressive layer 794. As indicated by the arrows, this collapse is radially inward. When the compressive layer 794 is subjected to negative pressure, the nested arrows of the second portion 862 of the second plurality of voids 842 collapse into each other and towards the second tapered end 806 along a contour of a perimeter of the compressive layer 794. As indicated by the arrows, this collapse is radially inward. The pattern of voids 822 is a thick-walled pattern of voids and can be used in a compressive layer material having a relatively low modulus of elasticity. The pattern of voids 822 is symmetric about the lateral axis 814 and the longitudinal axis 810. Accordingly, compression in the lateral and the longitudinal directions is symmetric about the lateral axis 814 and the longitudinal axis 810, respectively. In some embodiments, the compressive layer 794 can include a plurality of perforations similar to the plurality of perforation described above with respect to FIGS. 3-5.

Figure 20:
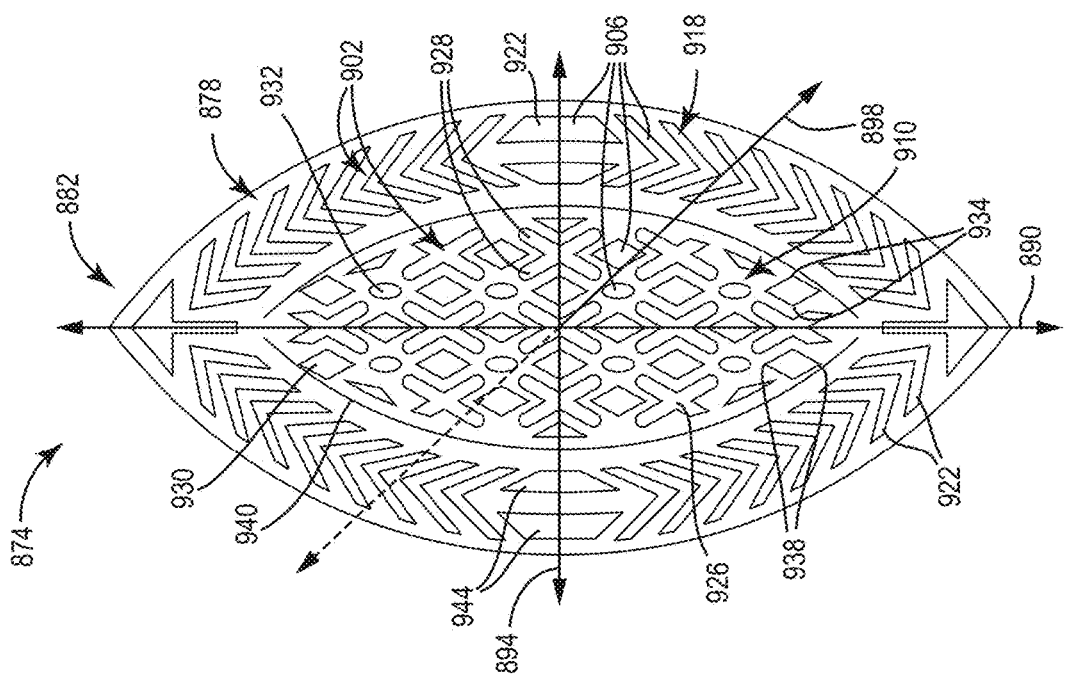
FIG. 20 is a front view of a compressive layer of a wound dressing of the wound therapy system of FIG. 1 according to some embodiments.

FIG. 20 illustrates a front view of a compressive layer 874 according to an another exemplary embodiment. The compressive layer 874 is shown to include a first surface 878 and a second, fascia-facing, surface (not shown) opposite the first surface 878. When the compressive layer 874 is applied to a wound, the first surface 878 faces away from the fascia 26 and the second surface faces toward the fascia 26. In some embodiments, the second surface of the compressive layer 874 contacts the first surface 878 of the visceral protective layer 42. In some embodiments, the first surface 878 of the compressive layer 874 contacts the sealing layer 50. The compressive layer 874 is shaped to conform to a shape of the open abdominal incision 22 so that the compressive layer 874 is configured to be positioned within the open abdominal incision 22. For example, as shown in FIG. 20, the compressive layer 874 has a generally elliptical shape having a first tapered end 882 and a second tapered end 886. The compressive layer 874 includes a longitudinal axis 890 defining a longitudinal direction, a lateral axis 894 defining a lateral direction, and a vertical axis 898 defining a vertical direction. The first tapered end 882 and the second tapered end 886 are substantially oriented along the longitudinal axis 890. The compressive layer 874 has similar dimensions to the compressive layers 78 and 186. For the sake of brevity, these dimensions are not further discussed herein.

As illustrated in FIG. 20, the compressive layer 874 includes a pattern of voids 902. The pattern of voids 902 is formed by a plurality of voids 906 (e.g., through holes) extending between the first surface 878 and the second surface similar to what is shown in FIGS. 4 and 9 for the compressive layers 46, 186, respectively. The plurality of voids 906 are oriented so that the plurality of voids 906 open in a direction that is generally parallel to the vertical axis 898. Accordingly, in the illustrated embodiment, the compression in the vertical direction is based on the pores. More specifically, the pattern of voids 902 includes a first pattern of voids 910 formed by a first plurality of voids 914 and a second pattern of voids 918 formed by a second plurality of voids 922. The first plurality of voids 914 is configured to facilitate lateral compression under negative pressure. The first pattern of voids 910 includes a plurality of generally X-shaped voids 926, a plurality of generally diamond-shaped voids 930, and a plurality of generally oval shaped voids 932. The plurality of X-shaped voids are positioned in rows that are generally parallel to the lateral axis 894 and columns that are generally parallel to the longitudinal axis 890. The plurality of diamond-shaped voids 930 and have a pair of obtuse vertices 934 and a pair of acute vertices 938. The first plurality of voids 914 are positioned so that the pairs of acute vertices 938 are positioned in rows that are generally parallel to the longitudinal axis 890 and the pairs of obtuse vertices 934 are positioned in rows that are generally parallel to the lateral axis 894. The plurality of diamond-shaped voids 930 are positioned adjacent the plurality of X-shaped voids 926 in between the legs 928 of the plurality X-shaped voids 926. The plurality of oval shaped voids 932 are positioned adjacent the plurality of diamond shaped voids 930. A plurality of slits 940 extends between the first pattern of voids 770 and the second pattern of voids 778.

The second plurality of voids 922 surrounds the first plurality of voids 914 and is configured to facilitate radial compression under negative pressure. The second plurality of voids 922 are shaped like nested arrows. A first portion of the second plurality of voids 922 are positioned on a first side of the lateral axis 894 includes nested arrows pointing to the first tapered end 882 of the compressive layer 874. A second portion of the second plurality of voids 922 positioned on a second side of the lateral axis 894 includes nested arrows pointing to the second tapered end 886 of the compressive layer 874. Under negative pressure conditions, the nested arrows of the first portion of the second plurality of voids 922 collapse into each other and towards the first tapered end 882 along a contour of a perimeter of the compressive layer 874. As indicated by the arrows, this collapse is radially inward. When the compressive layer 874 is subjected to negative pressure, the nested arrows of the second portion of the second plurality of voids 922 collapse into each other and towards the second tapered end 886 along a contour of a perimeter of the compressive layer 874. As indicated by the arrows, this collapse is radially inward. The second plurality of voids 844 further includes two pair of generally trapezoidal-shaped voids 944 spaced apart along the lateral axis 814. The thickness of the voids 870 is oriented along the lateral axis 814 to facilitate compression in the lateral direction. The pattern of voids 902 is symmetric about the lateral axis 894 and the longitudinal axis 890. The pattern of voids 902 is a thin-walled pattern of voids and can be used in a compressive layer material having a relatively high modulus of elasticity. Accordingly, compression in the lateral and the longitudinal directions is symmetric about the lateral axis 894 and the longitudinal axis 890, respectively. In some embodiments, the compressive layer 874 can include a plurality of perforations similar to the plurality of perforation described above with respect to FIGS. 3-5.

Figure 21:
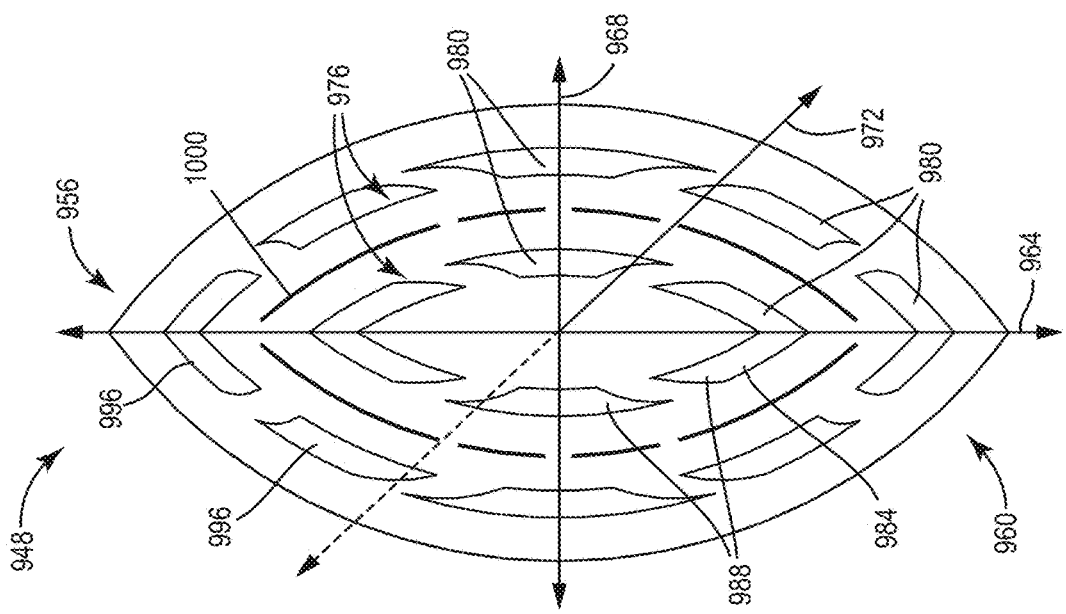
FIG. 21 is a front view of a compressive layer of a wound dressing of the wound therapy system of FIG. 1 according to some embodiments.

FIG. 21 illustrates a front view of a compressive layer 948 according to an another exemplary embodiment. The compressive layer 948 is shown to include a first surface 952 and a second, fascia-facing, surface (not shown) opposite the first surface 952. When the compressive layer 948 is applied to a wound, the first surface 952 faces away from the fascia 26 and the second surface faces toward the fascia 26. In some embodiments, the second surface of the compressive layer 948 contacts the first surface 952 of the visceral protective layer 42. In some embodiments, the first surface of the compressive layer 948 contacts the sealing layer 50. The compressive layer 948 is shaped to conform to a shape of the open abdominal incision 22 so that the compressive layer 948 is configured to be positioned within the open abdominal incision 22. For example, as shown in FIG. 21, the compressive layer 948 has a generally elliptical shape having a first tapered end 956 and a second tapered end 960. The compressive layer 948 includes a longitudinal axis 964 defining a longitudinal direction, a lateral axis 968 defining a lateral direction, and a vertical axis 972 defining a vertical direction. The first tapered end 956 and the second tapered end 960 are substantially oriented along the longitudinal axis 964. The compressive layer 948 has similar dimensions to the compressive layers 78 and 186. For the sake of brevity, these dimensions are not further discussed herein.

As illustrated in FIG. 21, the compressive layer 948 includes a pattern of voids 976. The pattern of voids 976 is formed by a plurality of voids 980 (e.g., through holes) extending between the first surface 952 and the second surface similar to what is shown in FIGS. 4 and 9 for the compressive layers 46, 186, respectively. The plurality of voids 980 are oriented so that the plurality of voids 980 open in a direction that is generally parallel to the vertical axis 972. Accordingly, in the illustrated embodiment, the compression in the vertical direction is based on the pores. More specifically, the pattern of voids 980 includes a first pattern of voids 984 formed by a first plurality of voids 988 and a second pattern of voids 992 formed by a second plurality of voids 996. The first plurality of voids 988 is configured to facilitate lateral compression under negative pressure. The first pattern of voids 984 includes a plurality voids generally shaped to follow a contour of the compressive layer 948. The first pattern of voids 984 is configured to facilitate a lateral and radially inward compression under negative pressure.

For example, the first pattern of voids 984 includes a pair of voids that is generally parallel to the longitudinal axis 964 that is configured to provide generally lateral contraction under negative pressure. The first plurality of voids 988 includes a second pair of voids that are generally v-shaped voids that follow a contour of the first tapered end 956 and the second tapered end 960. The pair of generally v-shaped voids is configured to collapse in a radially inward direction. As shown in FIG. 21, a majority of the thickness of the V-shaped voids is oriented along the lateral axis, so the radial collapse occurs more in a lateral direction than in a longitudinal direction. A plurality of slits 1000 extends between the first pattern of voids 770 and the second pattern of voids 778.

The second plurality of voids 996 surrounds the first plurality of voids 988 and is configured to facilitate radial compression under negative pressure. The second plurality of voids 996 is spaced from the first plurality of voids and follows a contour of the compressive layer 948. The first pattern of voids 984 is configured to facilitate a lateral and radially inward compression under negative pressure. For example, the second pattern of voids 992 includes a pair of voids that is generally parallel to the longitudinal axis 964 that is configured to provide generally lateral contraction under negative pressure. The second pattern of voids 992 includes a second plurality of voids that are angled toward towards one of the tapered ends 956, 960. The second pattern of voids 992 includes a third pair of voids that are generally v-shaped voids that follow a contour of the first tapered end 956 and the second tapered end 960. The pair of generally v-shaped voids is configured to collapse in a radially inward direction. As shown in FIG. 21, a majority of the thickness of the second plurality of voids 996 and the V-shaped voids is oriented along the lateral axis, so the radial collapse occurs more in a lateral direction than in a longitudinal direction. The pattern of voids 976 is a thick-walled pattern of voids and can be used in a compressive layer material having a relatively low modulus of elasticity. The pattern of voids 976 is symmetric about the lateral axis 968 and the longitudinal axis 964. Accordingly, compression in the lateral and the longitudinal directions is symmetric about the lateral axis 968 and the longitudinal axis 964, respectively. In some embodiments, the compressive layer 948 can include a plurality of perforations similar to the plurality of perforations described above with respect to FIGS. 3-5.

The Sealing Layer

Referring again to FIG. 1, the sealing layer 50 is shown to include a first surface 104 and a second, wound-facing, surface 108 opposite the first surface 104. When the wound therapy system 10 is applied to a wound, the first surface 104 faces away from the wound, whereas the second surface 108 faces toward the wound. As is shown in FIG. 1, at least a perimeter of the second surface 108 includes an adhesive. The adhesive is intended to adhere the sealing layer 50 to the patient's skin and to form a fluid-tight seal about the incision, generating a sealed space in the open abdomen. The sealing layer 50 also provides a barrier to passage of microorganisms through the wound therapy system 10. The negative pressure source (e.g., the pump 1010) can be fluidly coupled to the sealing layer 50 (and the sealed space) to provide negative pressure to the sealed space. For example, the negative pressure source (e.g., the pump 1010) may be fluidly coupled to the sealed space via tubing from the negative pressure source (e.g., the pump 1010) to an aperture in the sealing layer 50.

In some embodiments, the sealing layer 50 is an elastomeric material or may be any material that provides a fluid seal. "Fluid seal" means a seal adequate to hold pressure at a desired site given the particular reduced-pressure subsystem involved. The term "elastomeric" means having the properties of an elastomer and generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, thermoplastic polyurethane (TPU), and silicones. As non-limiting examples, the sealing layer 50 may be formed from materials that include a silicone, 3M Tegaderm® drape material, acrylic drape material such as one available from Avery, or an incise drape material.

The sealing layer 50 may be substantially impermeable to liquid and substantially permeable to water vapor. In other words, the sealing layer 50 may be permeable to water vapor, but not permeable to liquid water or wound exudate. This increases the total fluid handling capacity (TFHC) of wound therapy system 10 while promoting a moist wound environment. In some embodiments, the sealing layer 50 is also impermeable to bacteria and other microorganisms. In some embodiments, the sealing layer 50 is configured to wick moisture from the compressive layer 46 and distribute the moisture across the first surface 104. In some embodiments, the adhesive applied to the second surface 108 of the sealing layer 50 is moisture vapor transmitting and/or patterned to allow passage of water vapor therethrough.

In some embodiments, the adhesive layer 50 can include a NPWT port 1004 for establishing fluid communication with the NPWT system 54 and an instillation port 1008 for establishing fluid communication with an instillation system 58. The NPWT port 1004 is in fluid communication with the compressive layer 46. The instillation port 1008 is in fluid communication with an instillation conduit 1012 configured to transport instillation fluid to instillation pathways 1013 positioned within the visceral protective layer 42.

Deployment of the Wound Therapy System

Referring to FIGS. 1-2, FIG. 1 illustrates an exploded view of the wound therapy system 10 and FIG. 2 is a section view of the wound therapy system 10 deployed in an open abdominal incision 22 of a patient. The visceral protective layer 42 is positioned within the abdominal cavity to overlie the abdominal contents 18 and extend into the paracolic gutters 70, 74. The compressive layer 46 is then sized relative to the patient's abdominal incision 22. For embodiments such as the compressive layer 46 that include the plurality of perforations 106, portions of the compressive layer 46 proximate the plurality of perforations 106 may be torn or cut off so that the compressive layer 46 can fit within the abdominal incision 22. In other embodiments, the compressive layer 46 may be provided in a range of sizes, and an appropriate size compressive layer is selected. The compressive layer 46 is then oriented with respect to the abdominal incision 22 and the fascial incision 30, such that the longitudinal axis 90 of the compressive layer 46 is generally aligned with the fascial incision 30 and at least a portion of the compressive layer 46 extends over an intact (e.g., uncut) portion of the fascia 26. The compressive layer 46 is then positioned within the abdominal incision 22. The sealing layer 50 is then secured to the portion of the patient's skin that surrounds the abdominal incision 22 and is sealed to the patient's skin using the adhesive to form an air-tight seal around the abdominal incision. The NPWT system 54 is engaged with the NPWT port 1004 of the sealing layer 50. In some embodiments, the instillation system 58 is engaged with the instillation port 1008 of the sealing layer 50.

When the wound therapy system 10 has been secured to the abdomen as described above, the NPWT source of the NPWT system 54 is actuated to generate negative pressure in the abdominal cavity. The negative pressure brings the compressive layer 46 into frictional contact with the fascial layer 26 such that the fascia layer 26 moves, with respect to the abdominal contents 18, with the compressive layer 46. The suction force generated by the negative pressure source causes contraction of the compressive layer 46. More specifically, the suction first causes generally lateral and/or radial contraction of the compressive layer 46 while resisting generally vertical contraction of the compressive layer 46 and then causes generally vertical contraction of the compressive layer 46. The generally lateral and/or radial contraction of the compressive layer 46 occurs before the generally vertical contraction of the compressive layer 46 because the large size of the plurality of voids 110 relative to the pores means of the compressive layer material causes the voids to require less applied force to contract.

With reference to the compressive layer 46 shown in detail in FIGS. 3-5, in some embodiments the compressive layer 46 is configured to generate a combination of generally lateral and generally radially inward contraction of the fascial layer 26. Since the compressive layer 46 is frictionally engaged with the fascial layer 26, the lateral contraction of the compressive layer 46 pulls the intact portion of the fascial layer 26 proximate the fascial incision 22 laterally and/or radially inward towards the longitudinal axis 90, which in turn pulls the cut ends of the fascial layer 26 together based on the material properties of the compressive layer. For example, in the embodiment illustrated in FIGS. 3-5 and the embodiment illustrated in FIGS. 6-7, the pattern 102 of the compressive layer is configured to contract radially inward and pull the fascial layer 26 radially inward. In other embodiments, such as the embodiment illustrated in FIGS. 8-10, the pattern of the compressive layer is configured to contract laterally and pull the fascial layer laterally inward. In other embodiments, such as the embodiments illustrated in FIGS. 11-21, the compressive layer includes a first portion configured to contract laterally and a second portion surrounding the first portion configured to contract radially.

The compressive layer 46 overlies a portion of the intact portion of the fascial layer 26 and exerts a distributed force that is generally symmetric across the lateral axis 94 and the over both the intact portion of the fascial layer 26 and the ends of the fascial layer 26. The distributed force is exerted over a relatively large area and is therefore less likely to tear or otherwise damage the fascial layer 26 during contraction. This is in contrast to traditional methods of fascial closure, in which surgical tools are used to grasp the cut ends of the fascial layer 26 together and pull the cut ends of the fascial layer together. Such tools exert point forces on a relatively small portion of the cut ends of the fascial layer, which can lead to tearing of and/or other damage to the fascial layer 26. The negative pressure generated by the negative pressure source is strong enough to hold the cut ends of the fascia in close proximity during open abdomen conditions without the use of traditional closure methods such as staples or sutures. Accordingly, the fascial layer can be re-opened/reclosed as necessary for patient care without doing further damage to the fascia.

Fluid Removal

FIG. 1 illustrates the NPWT system 54 engaged with the wound treatment system 10. The NPWT system includes a pump 1010 configured to apply a negative pressure to the wound site and a removed fluid container 1012 to retain exudate from the wound site. In addition to providing NPWT, the negative pressure caused by the pump 1010 holds the cut ends of the facial incision 22 together, preventing retraction of the fascial layer 26 during open abdomen conditions.

As shown in FIG. 1, in some embodiments, the wound therapy system 10 includes the instillation system 58 having an instillation fluid source 1014. In such embodiments, the visceral protective layer 42 includes the instillation conduit 1012 engaged with a plurality of instillation pathways 1013. The instillation system 58 is actuable to dispense instillation fluid to the abdominal cavity to prevent drying out of the abdominal contents 18.

Felting Method

FIGS. 22-23 illustrate a felting process for generating an anisotropic compressive layer material. The felting process illustrated in FIGS. 22-23 can be done on a reticulated polyurethane foam material, such as the Granufoam® material discussed above. The compressive layer material can be used to form the compressive layers 46, 186, 246, 298, 478, 364, 422, 550, 666, 738, 794, 874, and 948 illustrated in FIGS. 3-21.

FIG. 22 illustrates a felting process for generating an anisotropic compressive layer material, such as the felted foam material discussed above. FIG. 20 illustrates an unfelted of material 1016 and a felted of material 1020. As shown in FIG. 22a, the unfelted material 1016 includes a height $H_1$, a length $L_1$, and a width $W_1$. In the illustrated embodiment, the unfelted material 1016 is isotropic and has the same material properties in a longitudinal direction defined by a longitudinal axis 1024, a lateral direction defined by a lateral axis 1028, and a vertical direction defined by a vertical axis 1032. As shown in the inset 1036, the material 1016 includes a plurality of pores 1040. The plurality of pores 1040 are generally spherical in shape and have uniform structure in the lateral direction, the longitudinal direction, and the vertical direction. The felting process is a thermoforming process in which the unfelted material 1016 is heated. The unfelted material 1016 is then compressed in the generally vertical direction, as indicated by the arrows 1044, to permanently deform the unfelted material 1016. In some embodiments, the permanent compression causes the pores 1040 to deform such that the pores 1040 compress in the generally vertical direction and elongate in at least the lateral direction as shown in FIG. 22b. More specifically, the compression causes the pores 1040 to collapse in the generally vertical direction, which increases a density of the foam layer in the vertical direction. As shown in FIG. 22c, the felted material 1020 includes a height $H_2$, a length $L_2$, and a width $W_2$. As a result of the vertical compression of the felting process, the height $H_2$ is smaller than the height $H_1$. In some embodiments, the length $L_2$ of the felted material 1020 can be longer than the length $L_1$ of the unfelted material 1016. In other embodiments, the length $L_2$ can be substantially the same as the length $L_1$. In the illustrated embodiment, the felted material 1020 is anisotropic and has different material properties in a longitudinal direction defined by a longitudinal axis 1048, a lateral direction defined by a lateral axis 1052, and/or a vertical direction defined by a vertical axis 1056. As shown in the insets 1060, 1064, the felted material 1020 includes a plurality of pores 1068. The plurality of pores 1068 have flattened and/or buckled as a result of the permanent deformation caused by the compression. Accordingly, the plurality of pores 1068 do not have a uniform structure/shape in the vertical direction, the lateral direction, and the longitudinal direction. The plurality of pores 1068 have a greater density in the vertical direction as a result of the permanent deformation. The permanent deformation has also generated a modulus of elasticity in the vertical direction that is different than a modulus of elasticity in the lateral direction and/or the longitudinal direction. As is best seen in FIG. 22, the plurality of pores 1068 are generally elongate in the lateral direction and have thicknesses extending in the vertical direction. Accordingly, the felting process has generated an anisotropic felted material 1020 that favorably collapses in the vertical direction. In some embodiments, the foam can be felted to have a firmness ranging between 3-7. A firmness ranging between 3-7 indicates that the reticulated polyurethane foam material has been compressed by between approximately a factor of 3 and approximately a factor of 7 (e.g., has a thickness of between approximately ⅓ and approximately ⅐ of the original thickness). In some embodiments, the foam can be felted to have firmness of 5.

FIG. 23 illustrates a process for forming an anisotropic compressive layer material configured to collapse in a lateral direction more than a vertical and/or a longitudinal direction. FIG. 23a illustrates a layer a compressive layer material 1072, such as the felted material 1020 formed in the process of FIG. 22. The compressive layer material 1072 is an anisotropic material and has different material properties in a longitudinal direction defined by a longitudinal axis 1076, a lateral direction defined by a lateral axis 1080, and/or a vertical direction defined by a vertical axis 1084. As shown in the inset 1088, the felted material 1072 includes a plurality of pores 1092 that are elongate in the lateral direction and have thicknesses that extend in the vertical direction, facilitating collapse in the generally vertical direction. The compressive layer material 1072 is cut into a plurality of strips 1096. The strips can have a width that is at least a width of the compressive layer 1104. The strips are then rotated 90 degrees to orient the strips 1096 as shown in FIG. 23b. As shown in the inset 1100, the pores are now elongate in a generally vertical direction and have thicknesses oriented along the lateral axis 1080, facilitating compression in the lateral direction. The strips 1096 of compressive layer material 1072 are then bonded together form a layer of compressive layer material 1072. In some embodiments, the strips 1096 are bonded together using and adhesive or by a process such as flame lamination. A compressive layer 1104 then cut out of the compressive layer material 1071, as is shown in phantom in FIG. 23. In some embodiments, the compressive layer 1104 can be used in the wound therapy system 10. In other embodiments, any of the patterns of voids 102, 226, 262, 318, 392, 442, 506, 578, 694, 762, 822, 902, and 976 described above with respect to FIGS. 3-21 can be cut into the compressive layer 1104.

Compressive Layer With Radial Manifold

FIGS. 24-27 illustrate exemplary embodiments of compressive layers for use with the wound therapy system 10. The compressive layer are shaped to be positioned within at least a portion of the abdominal incision, such as an incision formed as part of a vertical laparotomy. The compressive layer is configured to overlie a fascial incision formed proximate a bottom of the abdominal incision.

Figure 24:
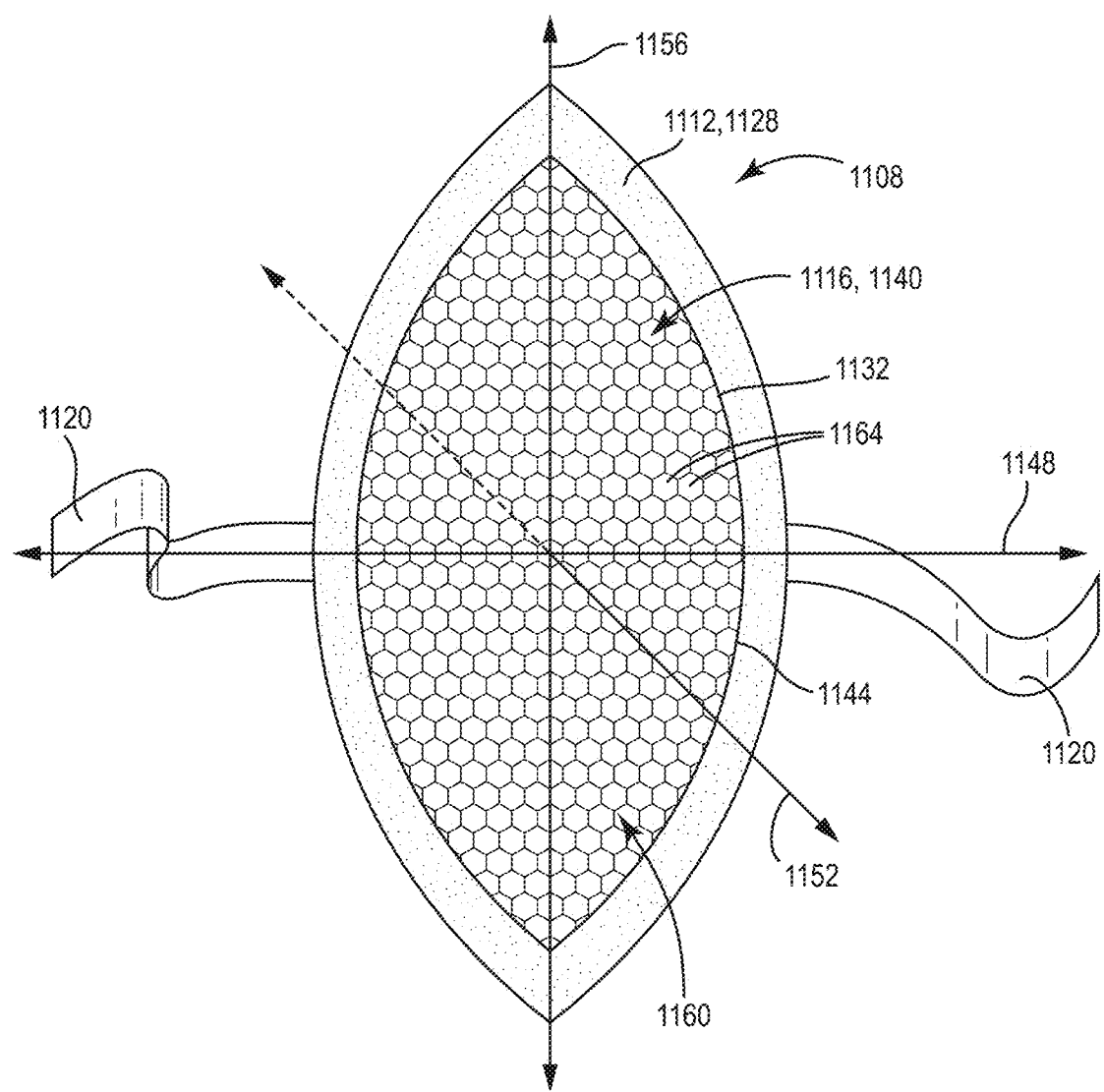
FIG. 24 illustrates a wound therapy system for a deep abdominal wound according to another embodiment.

As shown in FIG. 24, a compressive layer 1108 includes a foam manifold 1112, a compression portion 1116, and a plurality of optional straps 1120. The compressive layer 1108 includes a first surface 1124 (FIG. 25) and a second, fascia-facing surface 1128 opposite the first surface 1124. The second surface 1128 includes a cavity 1132 sized to receive the compression portion 1116. The foam manifold 1112 can be can be made from a porous and permeable foam-like material, such as the materials described previously with respect to the compressive layer 46. More particularly, a reticulated, open-cell polyurethane or polyether foam that allows good permeability of wound fluids while under a reduced pressure. One such foam material that has been used is the VAC® Granufoam® material that is available from Kinetic Concepts, Inc. (KCI) of San Antonio, Tex. Any material or combination of materials might be used for the compressive layer provided that the compressive layer is operable to distribute the reduced pressure and provide a distributed compressive force along the wound site. The foam manifold 1112 is adapted to wick fluid (e.g. exudate) from the wound and can include in-molded manifold structures for distributing negative pressure throughout the wound dressing 10 during NPWT treatments.

The compression portion 1116 includes a first surface 1136, a second, fascia-facing surface 1140 opposite the first surface 1136, and a sidewall 1144 surrounding a perimeter of the compression portion 1116. The compression portion 1116 can be positioned within the cavity 1132 of the foam manifold 1112, such that the first surface 1136 of the compression portion 1116 abuts the foam manifold 1112. The first surface 1136 and the sidewall 1144 are secured within the cavity 1132 of the foam manifold 1112. The compression portion 1116 is configured to facilitate compression in a lateral direction defined by a lateral axis 1148 and to resist compression in a vertical direction defined by a vertical axis 1152 and/or a longitudinal direction defined by a longitudinal axis 1156. The compression portion 1116 includes a pattern of voids 1160 formed by a plurality of voids 1164. The plurality of voids 1164 are oriented so that the plurality of voids 1164 open in a direction that is generally parallel to the vertical axis 1152. The pattern of voids 1160 is configured to collapse in a lateral direction under negative pressure. In the illustrated embodiment, the plurality of voids 1164 are hexagonally shaped. In other embodiments, the plurality of voids 1164 can be diamond-shaped or other geometric shapes. In some embodiments, the compression portion 1116 can be made of polymers such as polyethylene, polyvinyl chloride (PVC), or polyurethane.

In embodiments that include the optional plurality of straps 1120, the plurality of straps 1120 are secured to the second surface 1140 of the compression portion 1116. At least a portion of the plurality of straps 1120 includes an adhesive for attaching the abdominal wall. In some embodiments, the plurality of straps 1120 can be secured to the compression portion using a polyurethane and/or acrylic adhesive. The plurality of straps 1120 can be made of a lightweight, biocompatible fabric having a high tensile strength. In some embodiments, the plurality of straps 1120 can be made of a polyester fabric such as Prevena fabric by Miliken Chemical. The adhesive can be a generally high-tack, water resistant adhesive such as an acrylic or hydrocolloid adhesive. The plurality of straps 1120 secure the compression portion 1116 to the abdominal walls such that contraction of the compression portion 1116 in the presence of negative pressure causes contraction of the abdominal walls and pulls the cut ends of the fascial incision 22 together. In FIG. 24, the plurality of straps 1120 includes two straps 1120. However, in other embodiments, the plurality of straps 1120 can include more or fewer straps.

Figure 25:
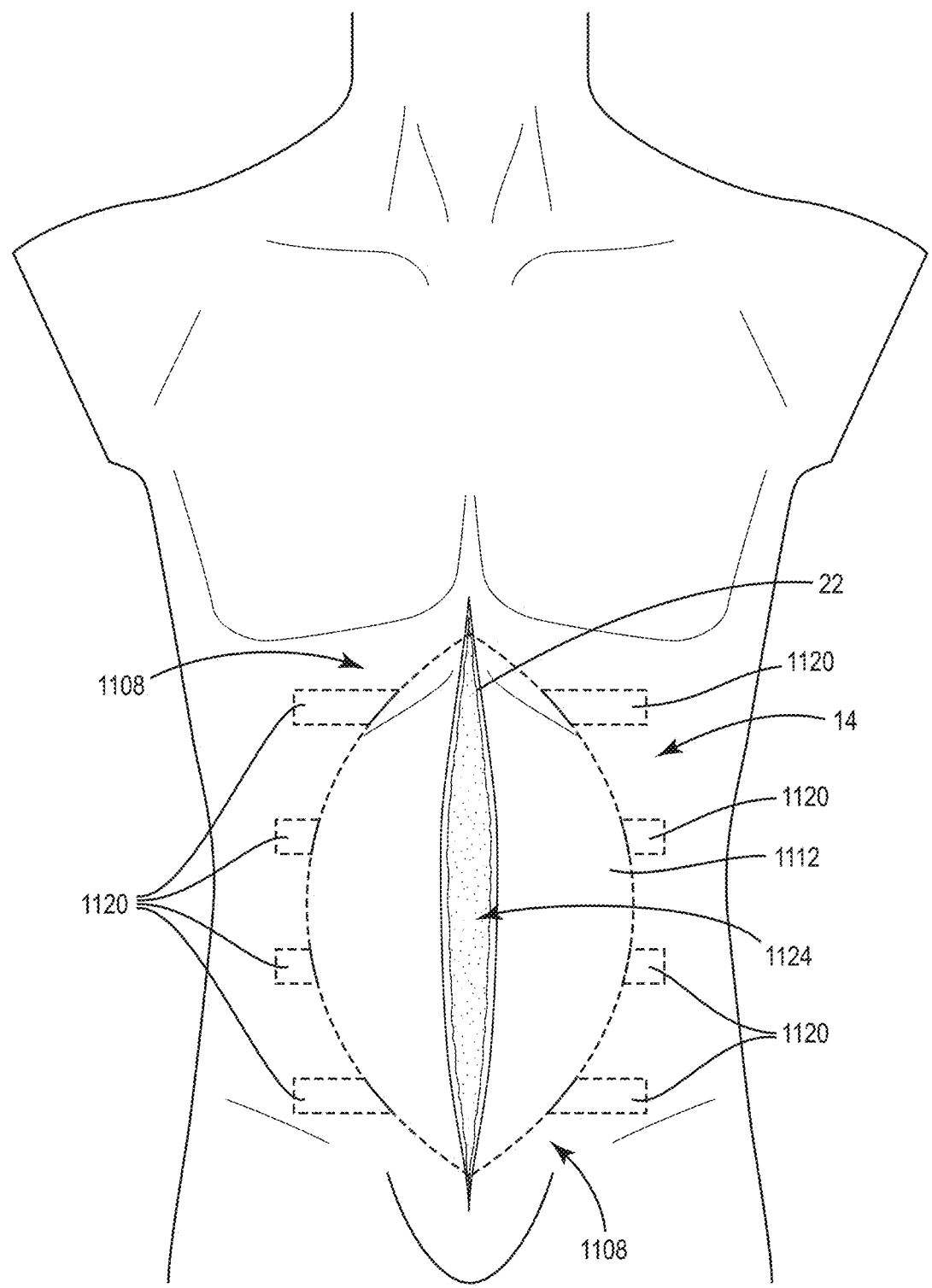
FIG. 25 illustrates the wound therapy system of FIG. 24 secured to an abdomen according to some embodiments.

FIG. 25 illustrates the compressive layer 1108 in an treatment orientation within the abdominal cavity. In the embodiment of FIG. 25, the plurality of straps 1120 includes four straps 1120. In other embodiments, the plurality of straps 1120 can include zero straps. The straps 1120 are oriented so that the straps 1120 can engage the abdominal wall. As illustrated in FIG. 25, the straps 1120 are secured to the walls of the abdominal cavity proximate the abdominal incision to transfer lateral contraction of the compression portion 1116 of the compressive layer 1108 to the abdominal walls.

Figure 26:
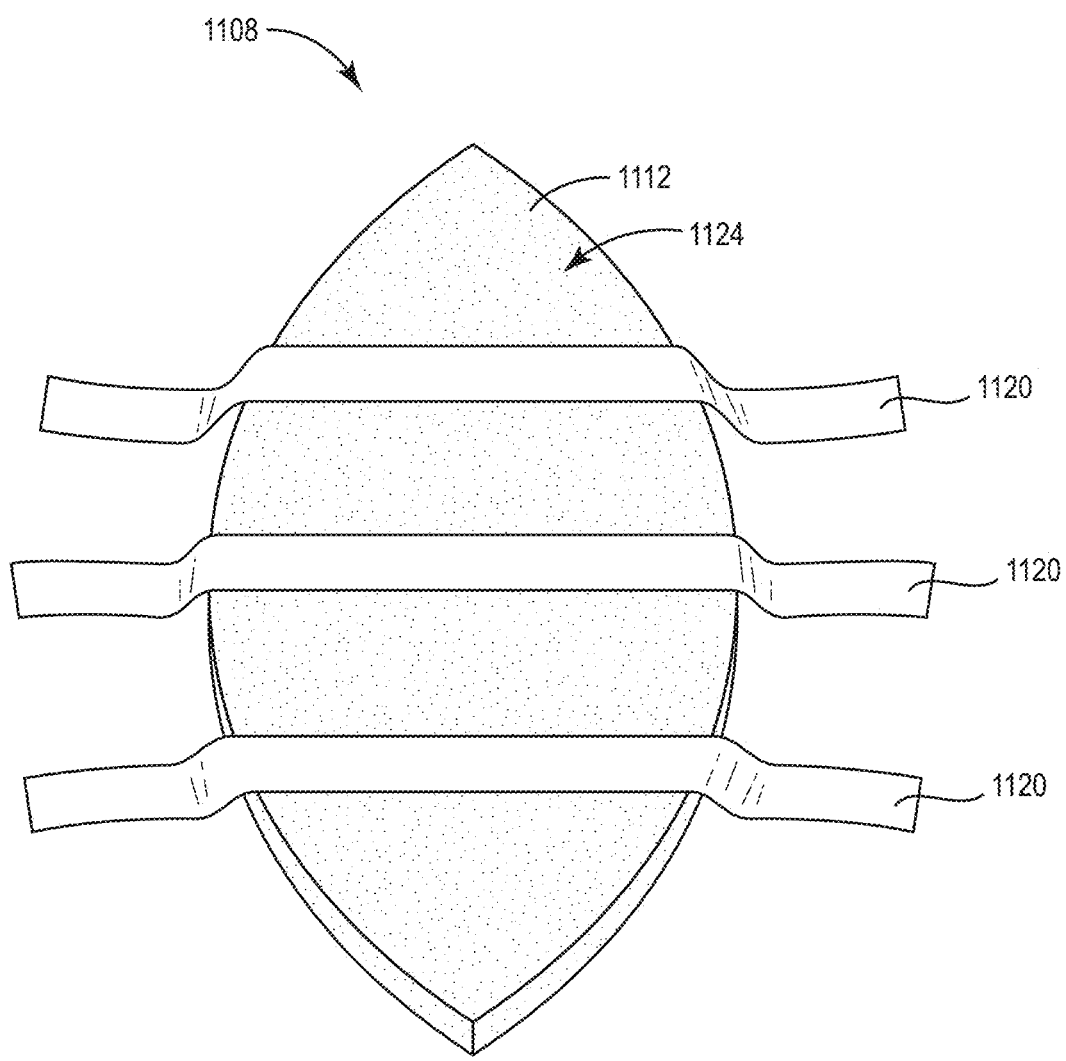
FIG. 26 illustrates a back view of the wound therapy system of FIG. 24 according to some embodiments.

FIG. 26 illustrates another deployment orientation of the compressive layer 1108. In the embodiment of FIG. 26, the plurality of straps 1120 includes three straps generally parallel to the lateral axis 1148 show in FIG. 24. In other embodiments, the plurality of straps 1120 can include zero straps. The straps 1120 are oriented such that the straps 1120 can adhere to the fascia and/or a visceral protective layer 42 abutting the fascial layer to transfer lateral contraction of the compression portion 1116 of the compressive layer 1108 to the fascia.

Figure 27:
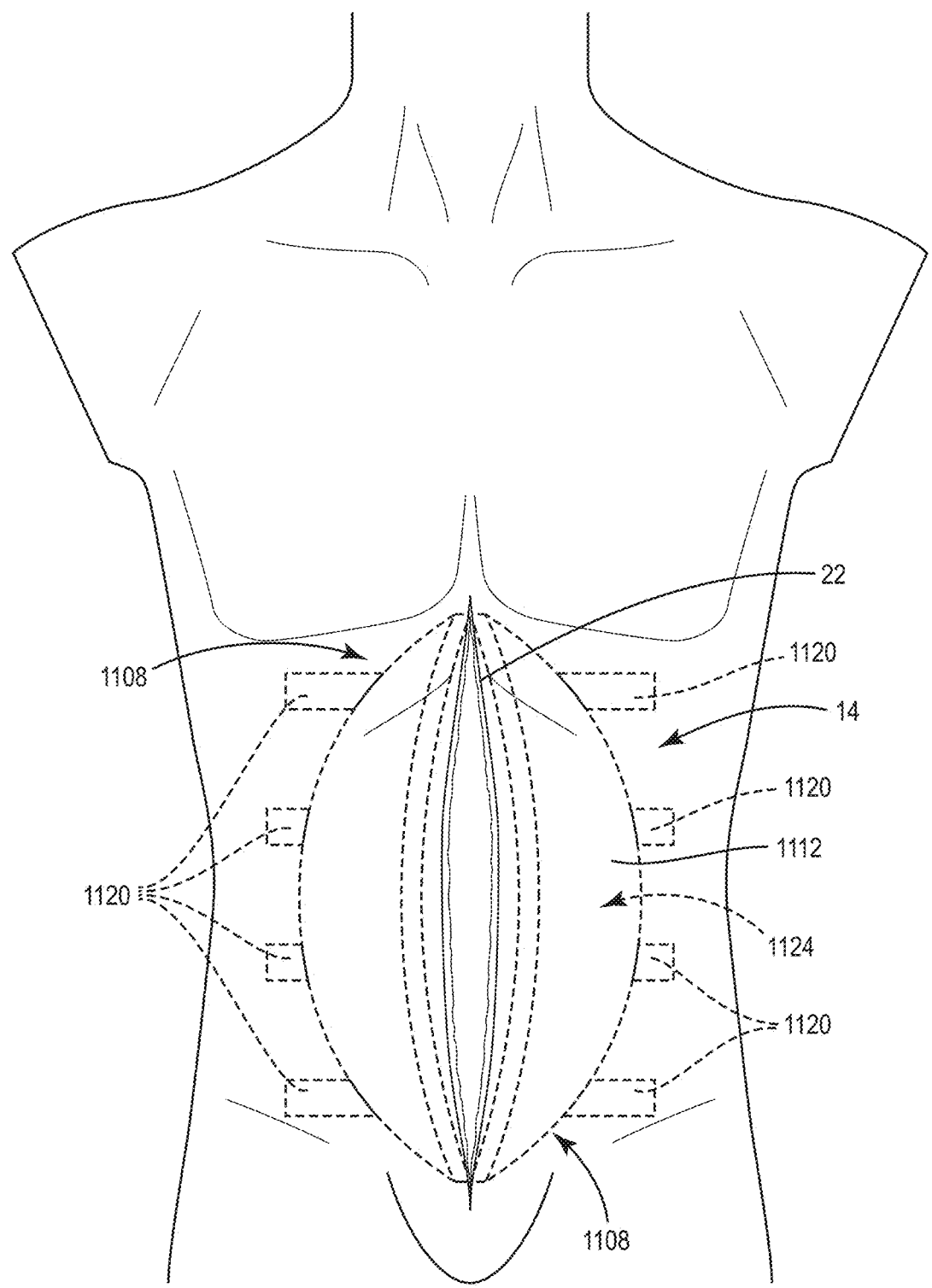
FIG. 27 illustrates the wound therapy system of FIG. 24 secured to an abdomen according to some embodiments.

FIG. 27 illustrates the compressive layer 1108 in an treatment orientation within the abdominal cavity. In the embodiment of FIG. 27, the plurality of straps 1120 includes four straps 1120. In other embodiments, the plurality of straps 1120 can include zero straps. The straps 1120 are oriented so that the straps 1120 can engage the abdominal wall. As illustrated in FIG. 25, the straps 1120 are secured to the walls of the abdominal cavity proximate the abdominal incision to transfer lateral contraction of the compression portion 1116 of the compressive layer 1108 to the abdominal walls. As shown in FIG. 27, the compressive layer 1108 has been cut to provide access to the abdominal cavity. For example, a physician may remove a portion of the compressive layer 1108 to suture the edges of the fascial layer together and to apply tension to the straps 1120. As a distance between the edges of the fascial edges decreases, more of the compressive layer 1108 can be removed.

Deployment of the Compressive Layer With Radial Manifold

The compressive layer 1108 can be used with the wound therapy system of FIGS. 1-2 instead of the compressive layer 46. The visceral protective layer 42 is positioned within the abdominal cavity to overlie the abdominal contents 18 and extend into the paracolic gutters 70, 74. An appropriate size of compressive layer 1108 is selected based on a size of the abdominal incision 22. The compressive layer 1108 is then oriented with respect to the abdominal incision 22 and the fascial incision 30, such that the longitudinal axis 1156 of the compressive layer 46 is generally aligned with the fascial incision 30 and at least a portion of the compressive layer 46 extends over an intact (e.g., uncut) portion of the fascia 26. The compressive layer 1108 is then positioned within the abdominal incision 22. The plurality of straps 1120 are then secured to the abdominal wall and/or the intact portions of the fascial layer 22. The sealing layer 50 is then secured to the portion of the patient's skin that surrounds the abdominal incision 22 and is sealed to the patient's skin using the adhesive to form an air-tight seal around the abdominal incision. The NPWT system 54 is engaged with the NPWT port 1004 of the sealing layer 50. In some embodiments, the instillation system 58 is engaged with the instillation port 1008 of the sealing layer 50.

When the wound therapy system 10 has been secured to the abdomen as described above, the NPWT source of the NPWT system 54 is actuated to generate negative pressure in the abdominal cavity. The suction force generated by the negative pressure source causes contraction of the compressive layer 1108, which is transferred to the abdominal walls and/or the fascial layer 22 by the plurality of straps 1120. More specifically, the suction first causes generally lateral contraction of the compressive layer 1108 while resisting generally vertical contraction of the compressive layer 1108 and then causes generally vertical contraction of the compressive layer 1108. The generally lateral and/or radial contraction of the compressive layer 1108 occurs before the generally vertical contraction of the compressive layer 1108 because the large size of the plurality of voids 1164 relative to the pores means of the compressive layer material causes the voids to require less applied force to contract. The negative pressure generated by the negative pressure source is strong enough to hold the cut ends of the fascia in close proximity during open abdomen conditions without the use of traditional closure methods such as staples or sutures. Accordingly, the fascial layer can be re-opened/reclosed as necessary for patient care without doing further damage to the fascia.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A system for treating a deep abdominal wound, the system comprising:
    a wound dressing including:
        a visceral-protective layer configured to be positioned in an open abdomen;
        a compressive layer configured to be disposed proximate to the visceral-protective layer, wherein the compressive layer comprising a pattern of voids that includes a first ring of voids and a second ring of voids, and a pattern of perforations that includes a first ring of perforations positioned between the first ring of voids and the second ring of voids; and
        a sealing layer configured to form a sealed space in the open abdomen; and
    a negative pressure source configured to provide negative pressure to the compressive layer.

2. The system of claim 1, wherein the pattern of voids is configured to collapse in a first direction and to resist collapse in a second direction substantially perpendicular to the first direction when subjected to the negative pressure.

3. The system of claim 2, wherein the compressive layer defines a longitudinal axis, and wherein the compressive layer is configured to collapse towards the longitudinal axis, thereby generating a lateral force towards the longitudinal axis.

4. The system of claim 3, wherein the first direction is a substantially lateral direction and the second direction is a substantially vertical direction, and wherein an amount of collapse in the first direction is greater than an amount of collapse in the second direction.

5. The system of claim 3, wherein the longitudinal axis is aligned with the fascial incision, and wherein the lateral force is configured to pull edges of the fascial incision towards the longitudinal axis.

6. The system of claim 3, wherein the pattern of voids is shaped to facilitate collapsing of the compressive layer towards the longitudinal axis.

7. The system of claim 2, wherein the pattern of voids surrounds at least a portion of a perimeter of the compressive layer, the pattern of voids shaped to facilitate radial inward collapsing of the compressive layer, thereby exerting a radial force towards a center of the compressive layer.

8. The system of claim 1, wherein the compressive layer defines a width and includes a tapered end extending from the width, and the compressive layer is configured to exert a first lateral compressive force proximate the width of the compressive layer and a second lateral force compressive force proximate the tapered end of the compressive layer, the first lateral compressive larger than the second lateral compressive force.

9. A system for treating a deep abdominal wound, the system comprising:
- a negative pressure source configured to provide a negative pressure;
- a wound dressing defining a longitudinal axis, the wound dressing including a compressive layer configured to resist compression in a direction normal to the wound dressing, the compressive layer including a pattern of voids, at least some of the voids having a concave surface and a convex surface, so that the convex surface follows a curved contour of the compressive layer and the concave surface faces toward the longitudinal axis, the pattern of voids configured to collapse in a greater amount in a substantially lateral direction than in a substantially vertical direction and a substantially longitudinal direction under the negative pressure, thereby exerting the a lateral compressive force towards the longitudinal axis.

10. The system of claim 9, wherein the pattern of voids is further configured to collapse in a radially inward direction under the negative pressure, thereby exerting the lateral compressive force towards the center of the wound dressing.

11. The system of claim 9, wherein a width of the wound dressing decreases along the longitudinal axis from the center of the wound dressing towards an end of the wound dressing, and wherein the dressing is configured to exert a larger lateral compressive force proximate the center of the body than proximate the end of the wound dressing.

12. The system of claim 9, wherein the longitudinal axis is configured to be aligned with a fascial incision, and wherein the lateral compressive force is configured to pull edges of the fascial incision towards the longitudinal axis.

* * * * *

UNITED STATES PATENT AND TRADEMARK OFFICE
CERTIFICATE OF CORRECTION

PATENT NO. : 11,040,127 B2  
APPLICATION NO. : 15/948376  
DATED : June 22, 2021  
INVENTOR(S) : Tyler H. Simmons Page 1 of 1

It is certified that error appears in the above-identified patent and that said Letters Patent is hereby corrected as shown below:

In the Claims

Column 37
Line 19, Claim 8, before "compressive" delete "force".

Column 38
Line 11, Claim 9, before "a lateral compressive" delete "the".

Signed and Sealed this
Twenty-third Day of April, 2024

Katherine Kelly Vidal
*Director of the United States Patent and Trademark Office*